United States Patent
Siegel

(10) Patent No.: US 10,626,722 B2
(45) Date of Patent: Apr. 21, 2020

(54) SYSTEM AND METHOD TO INCREASE LANDFILL GAS QUALITY FOR BENEFICIAL USE

(71) Applicant: ARC Technologies Corp., Yukon, PA (US)

(72) Inventor: Stanley Siegel, West Newton, PA (US)

(73) Assignee: ARC TECHNOLOGIES CORP., Yukon, PA (US)

( * ) Notice: Subject to any disclaimer, the term of this patent is extended or adjusted under 35 U.S.C. 154(b) by 317 days.

(21) Appl. No.: 15/669,706

(22) Filed: Aug. 4, 2017

(65) Prior Publication Data

US 2018/0038227 A1  Feb. 8, 2018

Related U.S. Application Data

(60) Provisional application No. 62/370,882, filed on Aug. 4, 2016.

(51) Int. Cl.
| | |
|---|---|
| E21B 49/08 | (2006.01) |
| B09B 1/00 | (2006.01) |
| E21B 47/00 | (2012.01) |
| E21B 43/00 | (2006.01) |
| G01N 33/00 | (2006.01) |

(52) U.S. Cl.
CPC .............. *E21B 49/08* (2013.01); *B09B 1/006* (2013.01); *E21B 43/00* (2013.01); *E21B 47/00* (2013.01); *G01N 33/0036* (2013.01)

(58) Field of Classification Search
CPC . B09B 1/00; B09B 1/006; E21B 47/00; E21B 49/08; E21B 43/00; G01N 33/0009; G01N 33/0036
See application file for complete search history.

(56) References Cited

U.S. PATENT DOCUMENTS

| | | | | | |
|---|---|---|---|---|---|
| 4,890,672 | A | * | 1/1990 | Hall | B09B 1/00 166/250.01 |
| 2011/0231099 | A1 | * | 9/2011 | Elkins | B09B 1/00 702/12 |
| 2012/0276616 | A1 | * | 11/2012 | Siegel | B01D 53/75 435/262 |
| 2017/0218732 | A1 | * | 8/2017 | Campanella | E21B 43/12 |

* cited by examiner

*Primary Examiner* — Carib A Oquendo

(57) ABSTRACT

The invention provides a method for efficiently adjusting existing landfill gas well head control devices in a manner which reduces the overall air migration into the landfill's gas collection systems in a short period of time. The method also provides for mapping out hydrogen sulfide concentration areas of landfills; allowing for efficient evaluation and selective reduction of hydrogen sulfide.

20 Claims, 26 Drawing Sheets

Predicted Curve Data

| | | 1. Primary Curve | 2. Auto Speed |
|---|---|---|---|
| CANISTER | Model | ZM 8803 | |
| | Configuration | (1) 8812 | (1) 8812 |
| | Impeller 1 | (1) 8821 | (1) 8821 |
| | Impeller 2 | (1) 8811 | (1) 8811 |
| | Impeller 3 | | |
| | Driver | | |
| | Control Method | | |
| CONDITIONS | Op. Speed RPM | 2,575 | 2,963 |
| | Inlet Throttling deg. open | none | none |
| | Bar. Pressure PSIA | 14.319 | 14.319 |
| | Disch. Pressure "HG | 100.00 | 100.00 |
| | Inlet Temp. °F | 100.0 | 100.0 |
| | Inlet Humidity % RH | 100.0 | 100.0 |
| | MW / k / Cp | 29.140/1.267/0.3235 | 29.140/1.267/0.3235 |
| PERFORMANCE | Volume (Std.) SCFM/gear | 1075.0 | 2200.0 |
| | Volume (Inlet) CFM | 1370.3 | 2822.7 |
| | Inlet Vacuum "HG | 40.00 | 40.00 |
| | Diff. P. "HG | 50.00 | 50.00 |
| | Power (Shaft) BHP | 15.93 | 34.38 |
| | Efficiency % | 68.02 | 60.75 |
| | Disch. Temp. °F | 122.07 | 125.46 |
| | Pressure Rise "HG | 0.26 | 14.68 |
| | Turndown % | 32.02 | 63.32 |
| SURGE | Surge Pressure "HG | 50.26 | 64.08 |
| | Surge Volume SCFM | 720.1 | 887.0 |

FIG. 25

SYSTEM AND METHOD TO INCREASE LANDFILL GAS QUALITY FOR BENEFICIAL USE

The current application claims a priority to the U.S. Provisional Patent application Ser. No. 62/370,882 filed on Aug. 4, 2016.

FIELD OF THE INVENTION

The present invention relates to air migration into a landfill gas (LFG) collection system and the systematic reduction of the air and hydrogen Sulfide (H2S) to allow for beneficial use of the landfill gas.

BACKGROUND OF THE INVENTION

Air migration into landfill gas collection systems is the number one issue that prevents more than 75% of all landfills from being candidates for beneficial use renewable fuels projects. Enhancing landfill gas quality for beneficial use as a renewable fuel or renewable natural gas (RNG) allows the landfill owner to receive enhanced revenue for their gas and reduces carbon dioxide (CO2), nitrogen oxide (NOx), and sulfur oxide (SOx) created by the unnecessary oxidation of the landfill gas by a landfill flare.

Landfill gas combustion engines for electric generation are limited to the percentage of oxygen in the fuel they burn. High oxygen (O2) results in engines failing and high repair costs. Landfill gas engines are more sensitive to O2 ingress from the gas collection system than flares such that engines may be programmed to shut down if O2 exceeds 2%. Proactive operators of the landfill gas collection systems are therefore required to minimize O2 within the incoming landfill gas. Typically, when landfill methane concentrations are reduced, the air intake flow rate (oxygen) to the engine increases and combustion temperatures rise. Landfill gas's oxygen concentration during the combustion process could vary having the potential to impact emissions and if engine's control system does not have the automatically adjustments the landfill engine could be in violation of the landfill's air permit.

Existing landfill gas upgrade technologies refine landfill gas to meet pipeline quality and compressed natural gas (CNG), but are limited by the amount of air that is contained in the raw landfill gas. This limitation comes in three forms 1) increased equipment capital cost to treat excess air (oxygen and nitrogen), 2) existing technology operating cost, and 3) safety limits on the amount of oxygen a system can handle.

High oxygen concentrations in landfill gas possess a safety problem dealing with all the usages of landfill gas; even flaring the landfill gas has its limitations.

The process of flaring, burning or engine combusting converts hydrogen Sulfide (H2S) to SOx. All landfills produce H2S gas with concentrations from 50 ppm to 2000 ppm or more. All of the landfill gas technologies usages have their limitations in handling the H2S concentration that they can process. Even flaring high (>500 ppm) concentrations of H2S is limited in populated areas in the world which mandate a pre-flare H2S process treatment system. There is a great need to control and manage the amount of H2S that is being pulled from a landfill to reduce costs of H2S treatment and reduce SOx emissions. Prior Art teaches no effective system and method to solve the problem to manage the concentration of H2S inside of a landfill.

It is an object of this invention to provide a system and method for onsite controlled analytical testing, well head tuning and technician training to quickly improve the quality of the landfill gas in regard to the reduction of air in the total landfill gas flow. It is a further object of the present invention to map out concentrations of H2S areas of landfills; allowing for efficient evaluation and selective reduction of H2S. Another object of the present invention is to evaluate landfills for potential renewable gas projects to confirm actual landfill gas flow, gas quality and existing landfill gas contaminates.

BRIEF DESCRIPTION OF THE DRAWINGS

FIG. 25 is a result table showing the performance primary and auto speed curve of the blower motor within the system of the present invention.

DETAIL DESCRIPTIONS OF THE INVENTION

All illustrations of the drawings are for the purpose of describing selected versions of the present invention and are not intended to limit the scope of the present invention.

Figure 1:
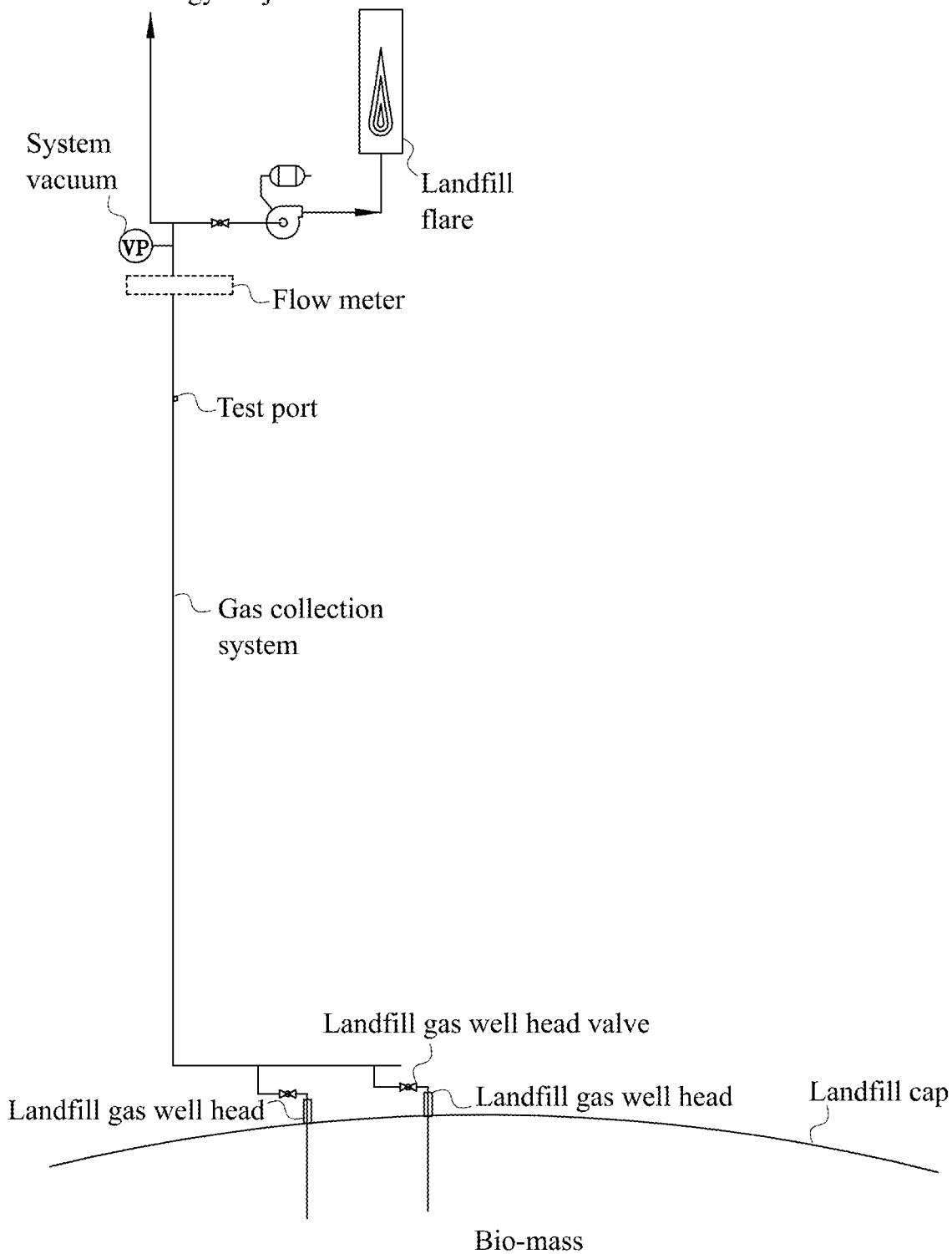
FIG. 1 is a system view that the present invention is implemented.

The present invention is a method of reducing air intrusion from existing landfill gas collection system. In reference to general concept, a plurality of landfill gas wells is drilled and installed into an existing landfill so that the plurality of landfill gas wells can extract landfill gas which is then gathered into a gas collection system for further processing, wherein the plurality of landfill gas wells is in fluid communication with the gas collection system. The collected landfill gas is then treated and processed to extract methane gas to produce electricity, heat, fuels, and various chemical compounds as shown in FIG. 1.

Figure 2:
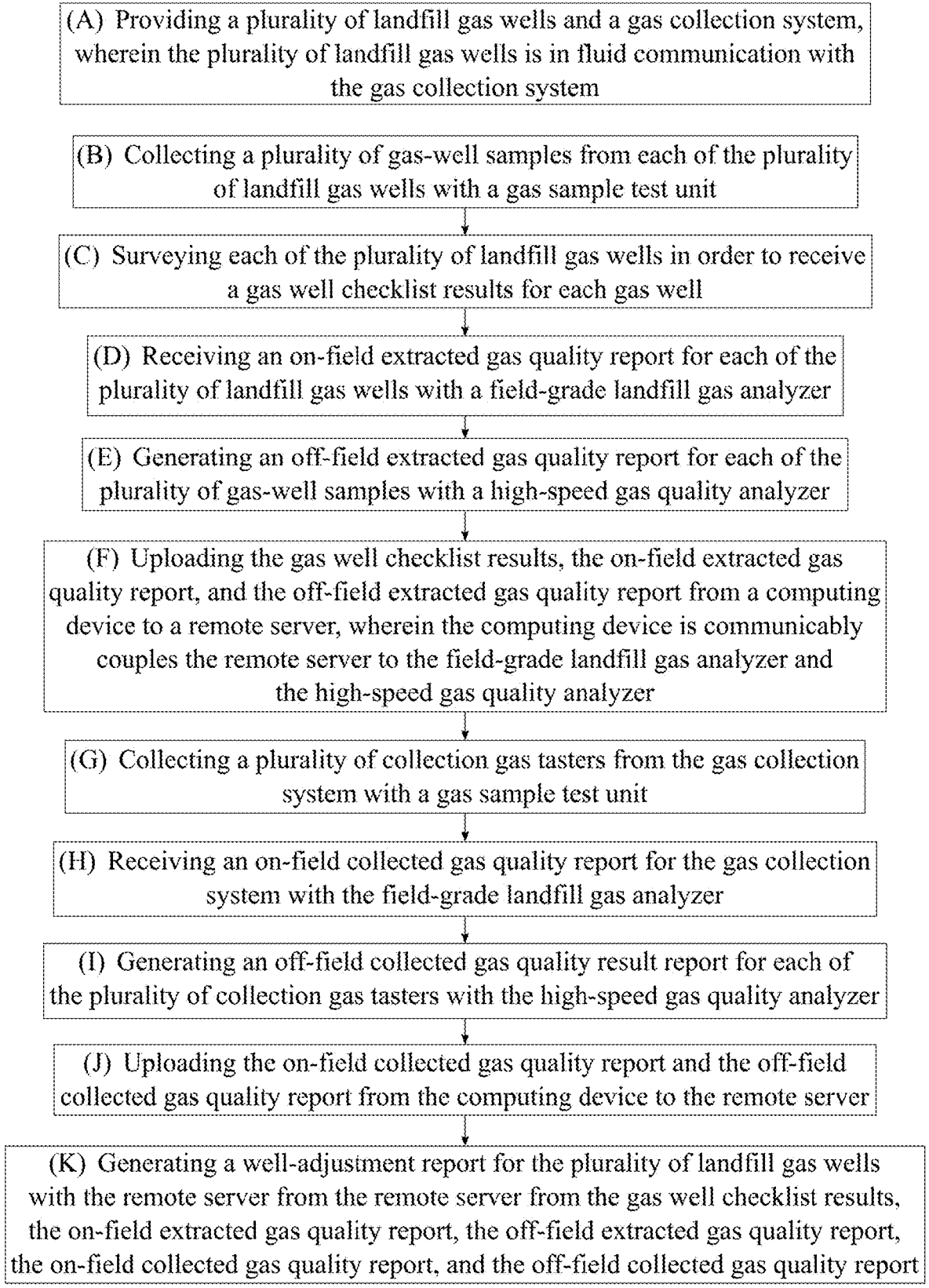
FIG. 2 is a flow chart for an overall method of the present invention.

In reference to FIG. 2, the plurality of gas-well samples is collected from each of the plurality of landfill gas wells by utilizing a gas sample test unit. More specifically, industry standard test units are utilized as the gas sample test unit so that plurality of gas-well samples can be collected for further testing of the landfill gas with respect to each of the plurality of landfill gas wells.

Figure 3:
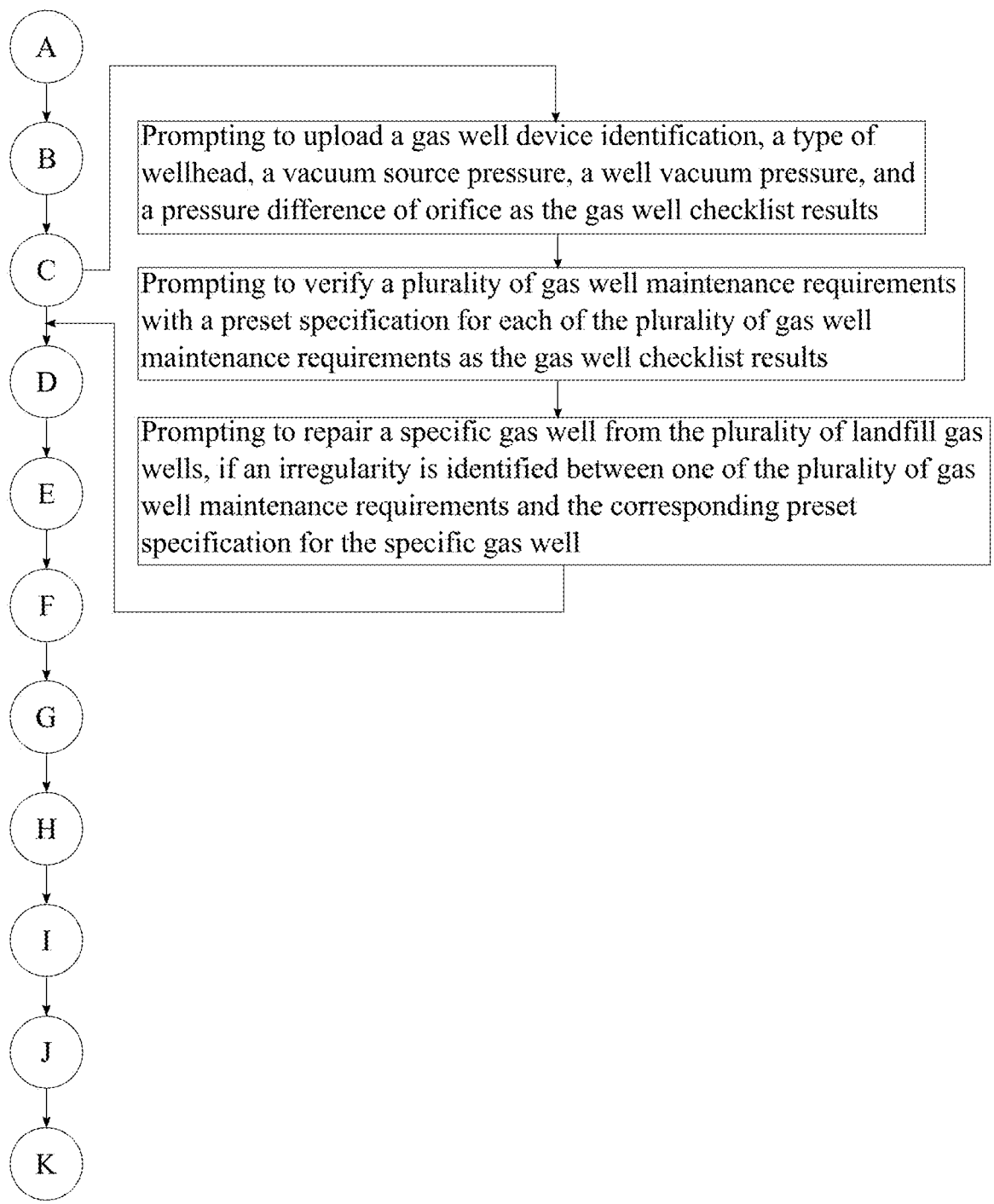
FIG. 3 is a flow chart for the surveying of the plurality of landfill gas well within the overall method of the present invention.

In reference to FIG. 2-3, each of the plurality of landfill gas wells is individually surveyed according to a gas well check list so that the present invention is able to obtain a gas well checklist results for each gas well. More specifically, the present invention prompts to upload a gas well device identification, a type of wellhead, a vacuum source pressure, a well vacuum pressure, and a pressure difference of orifice as the gas well checklist results so that numerical outputs that are normally associated with each landfill gas well can be obtained. Furthermore, the present invention prompts to verify a plurality of gas well maintenance requirements that are stated within the gas well check list. The plurality of gas well maintenance requirements include "yes" or "no" questions or multiple-choice questions so that the present invention can ensure the optimal functionality of each landfill gas well. For example, the plurality of gas well maintenance requirements can include, but are not limited to, the physical condition of the vacuum hose, is all the hardware units are secured? is there any gas leaks? and if there are any gas leaks, is it fixed temporary or permanently? Additionally, a preset specification for each of the plurality of gas well maintenance requirements is listed or notified within the gas well checklist results so that the present invention is able to identify an irregularity between one of the plurality of gas well maintenance requirements and the corresponding preset specification. More specifically, if the irregularity is identified between one of the plurality of gas well maintenance requirements and the corresponding preset specification for a specific gas well of the plurality of landfill gas wells, the present invention prompts to repair the specific gas well with an industry standard tool kit. Resultantly, the present invention can ensure the functionality of each landfill gas well.

Figure 4:
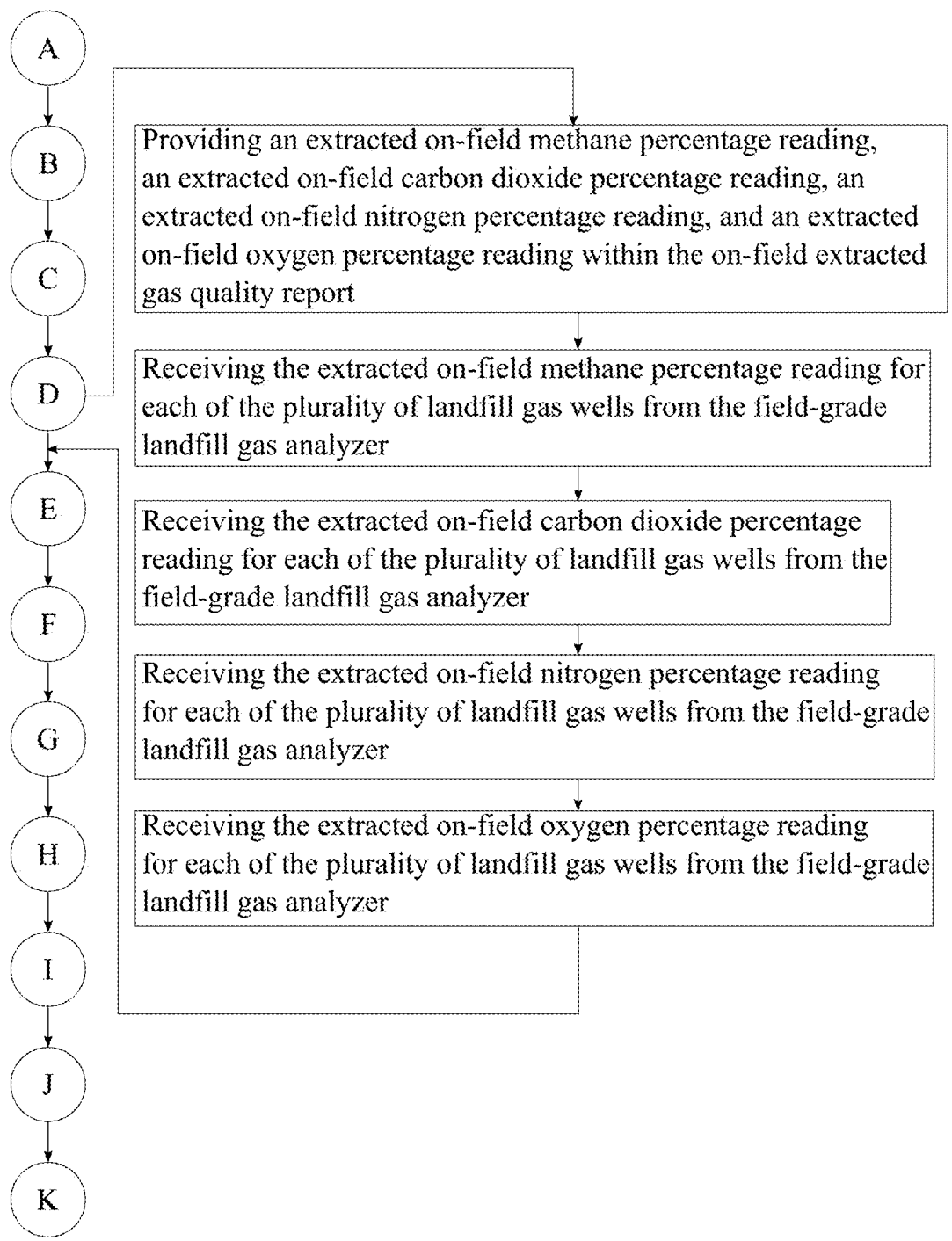
FIG. 4 is a flow chart for the receiving the on-field extracted gas quality report within the overall method of the present invention.

In reference to FIG. 2 and FIG. 4, the present invention then receives an on-field extracted gas quality report for each of the plurality of landfill gas wells with a field-grade landfill gas analyzer. The field-grade landfill gas analyzer can be any type of industry standard gas analyzer as long as it is able to provide a gas quality report. The on-field extracted gas quality report includes an extracted on-field methane percentage reading, an extracted on-field carbon dioxide percentage reading, an extracted on-field nitrogen percentage reading, and an extracted on-field oxygen percentage reading as each one of those readings represents an individual output in relation to each landfill gas well within the present invention. More specifically, when the field-grade landfill gas analyzer is coupled to each landfill gas well, the present invention is able to receive the extracted on-field methane percentage reading for each of the plurality of landfill gas wells, the extracted on-field carbon dioxide percentage reading for each of the plurality of landfill gas wells, the extracted on-field nitrogen percentage reading for each of the plurality of landfill gas wells, and the extracted on-field oxygen percentage reading for each of the plurality of landfill gas wells.

Figure 5:
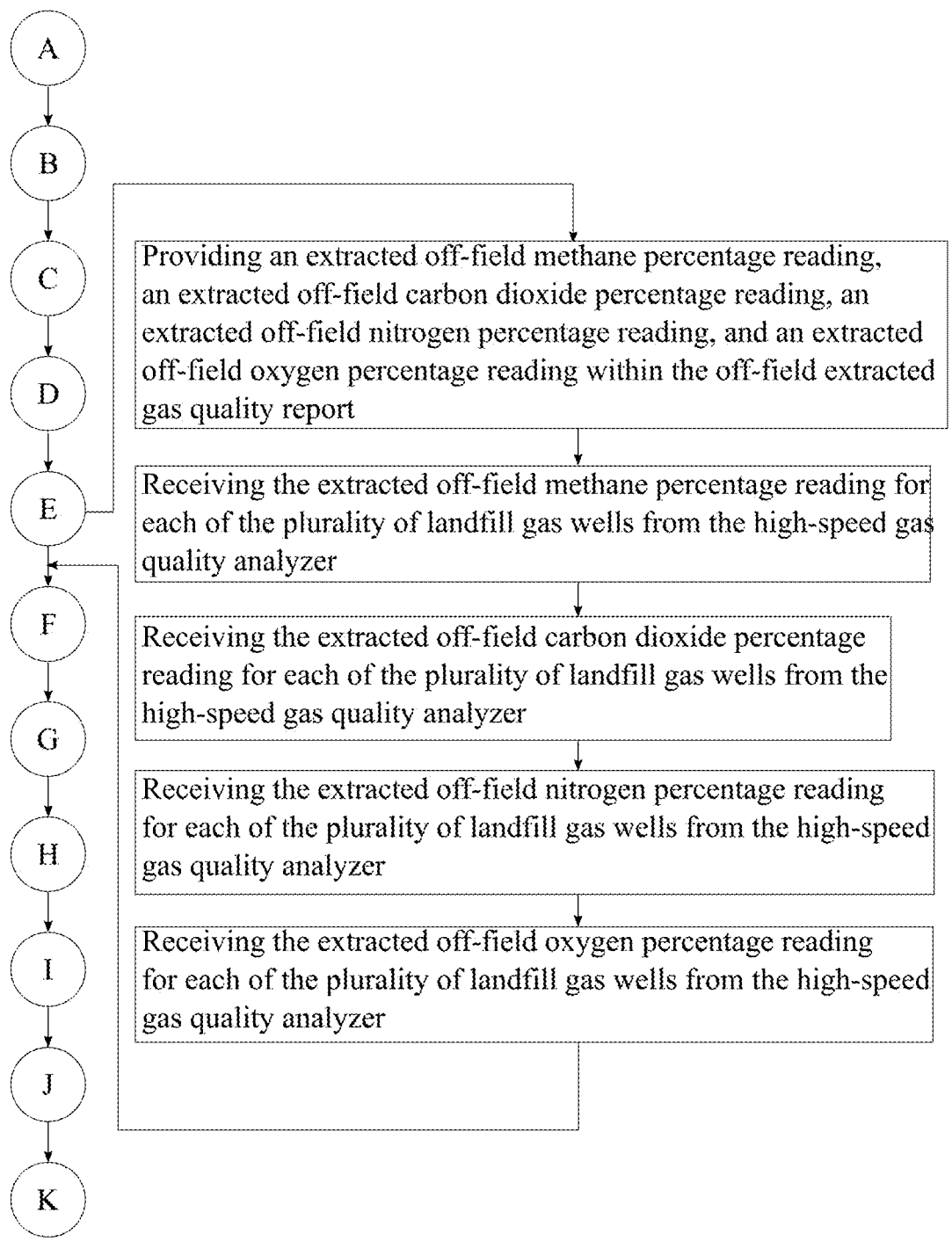
FIG. 5 is a flow chart for the generating the off-field extracted gas quality report within the overall method of the present invention.

In reference to FIG. 2 and FIG. 5, the present invention then generates an off-field extracted gas quality report for each of the plurality of gas-well samples. More specifically, the plurality of gas-well samples that is collected from each of the plurality of landfill gas wells is processed through a high-speed gas quality analyzer so that the present invention is able to attain an accurate gas quality report in comparison to the gas quality report received from the field-grade landfill gas analyzer. The off-field extracted gas quality report includes an extracted off-field methane percentage reading, an extracted off-field carbon dioxide percentage reading, and an extracted off-field nitrogen percentage reading as each one of those readings represents an individual output in relation to each landfill gas well. More specifically, when the plurality of gas-well samples is processed through the high-speed gas quality analyzer, the present invention is able to receive the extracted off-field methane percentage reading for each of the plurality of landfill gas wells, the extracted off-field carbon dioxide percentage reading for each of the plurality of landfill gas wells, the extracted off-field nitrogen percentage reading for each of the plurality of landfill gas wells, and the extracted off-field oxygen percentage reading for each of the plurality of landfill gas wells.

In reference to FIG. 2, the present invention uploads the gas well checklist results, the on-field extracted gas quality report, and the off-field extracted gas quality report to a remote server from a computing device. In reference to the network configuration, the computing device communicably couples the remote server to the field-grade landfill gas analyzer and the high-speed gas quality analyzer thus enabling the uploading process of the gas well checklist results, the on-field extracted gas quality report, and the off-field extracted gas quality report.

In reference to FIG. 2, the plurality of collection gas testers is collected from the gas collection system by utilizing a gas sample test unit. More specifically, industry standard test units are utilized as the gas sample test unit so that plurality of collection gas testers can be collected for further testing of the landfill gas with respect to the gas collection system.

Figure 6:
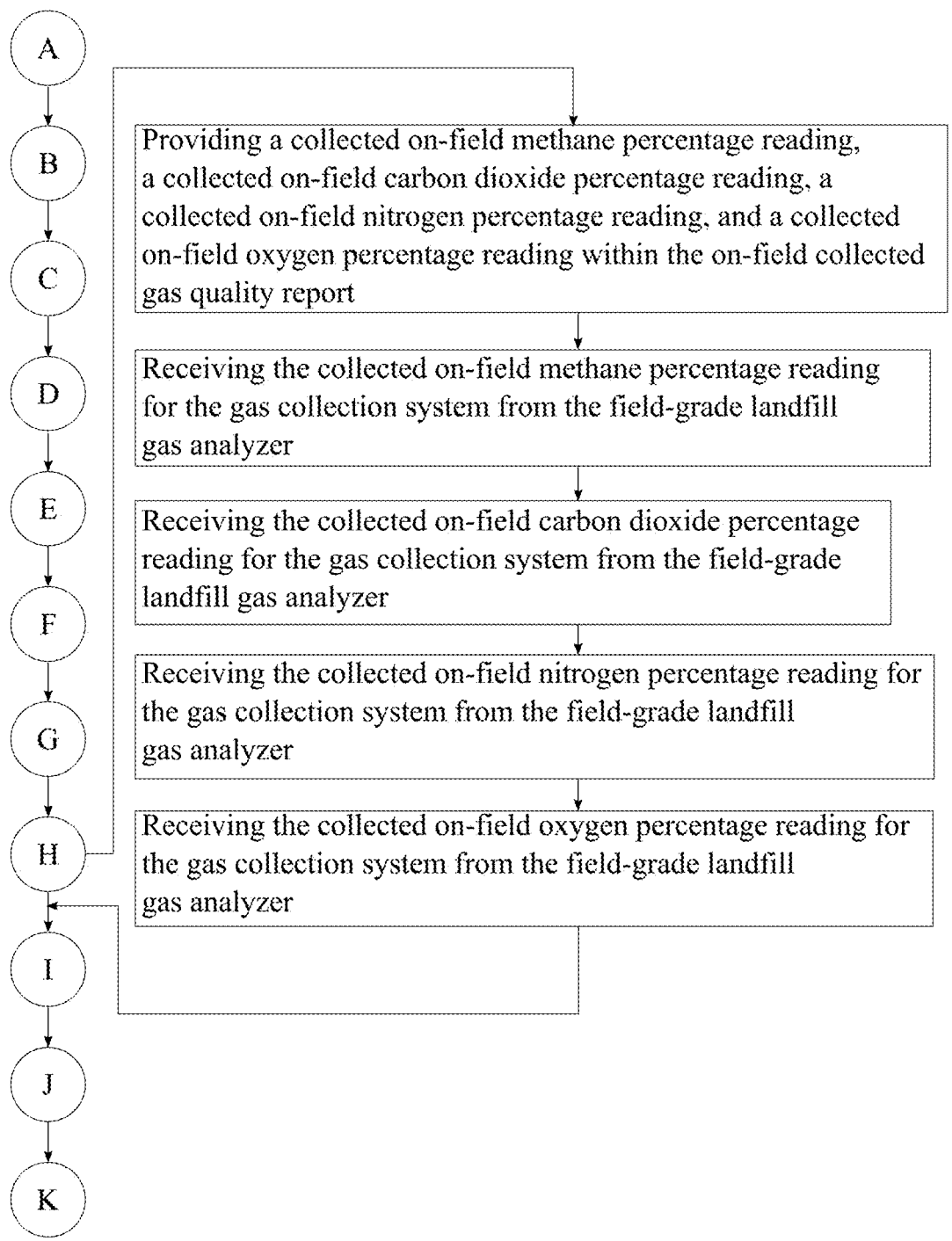
FIG. 6 is a flow chart for the receiving the on-field collected gas quality report within the overall method of the present invention.

In reference to FIG. 2 and FIG. 6, the present invention then receives an on-field collected gas quality report for the gas collection system with the field-grade landfill gas analyzer. The field-grade landfill gas analyzer can be any type of industry standard gas analyzer as long as it is able to provide a gas quality report. The on-field collected gas quality report includes a collected on-field methane percentage reading, a collected on-field carbon dioxide percentage reading, a collected on-field nitrogen percentage reading, and a collected on-field oxygen percentage reading as each one of those readings represents an overall output of the landfill gas within the present invention. More specifically, when the field-grade landfill gas analyzer is coupled to the gas collection system, the present invention is able to receive the collected on-field methane percentage reading for the gas computing device, wherein the computing device is able to complete the uploading process of the on-field collected gas quality report and the off-field collected gas quality report.

In reference to FIG. 2, the present invention then generates a well-adjustment report for the plurality of landfill gas wells with the remote server. More specifically, the well-adjustment report is generated upon the on-field extracted gas quality report, the off-field extracted gas quality report, the on-field collected gas quality report, and the off-field collected gas quality report. Due to the complex design and configuration of the high-speed gas quality analyzer, the high-speed gas quality analyzer provides an accurate readings compare to the field-grade landfill gas analyzer. In order to overcome this industry wide problem, the present invention calculates a correction factor that can be applied to the field-grade landfill gas analyzer. Due to fact that the field-grade landfill gas analyzer assumes nitrogen is always balance, calculates gas tolerance, is used as a standard for compliance reasons, and does not qualify as a gas custody measurement device, the high-speed gas analyzer outputs more accurate readings. Following is an example for the calculation of the correction factor within the present invention:

| Date/time | | | | | |
|---|---|---|---|---|---|
| Jun. 24, 2016 1:50 PM | High-speed gas quality analyzer | 45 | 36.6 | 16.4 | 1.76 |
| Jun. 24, 2016 1:50 PM | Field-grade landfill gas analyzer | 48.7 | 38.3 | 12.1 | 0.9 |
| | $\dfrac{\text{High speed gas quality analyzer}}{\text{Fieldgrade landfill gas analyzer}} = \text{correction factor}$ | 0.924025 | 0.955614 | 1.355372 | 1.9555 | collection system, the collected on-field carbon dioxide percentage reading for the gas collection system, the collected on-field nitrogen percentage reading for the gas collection system, and the collected on-field oxygen percentage reading for the gas collection system.

Figure 7:
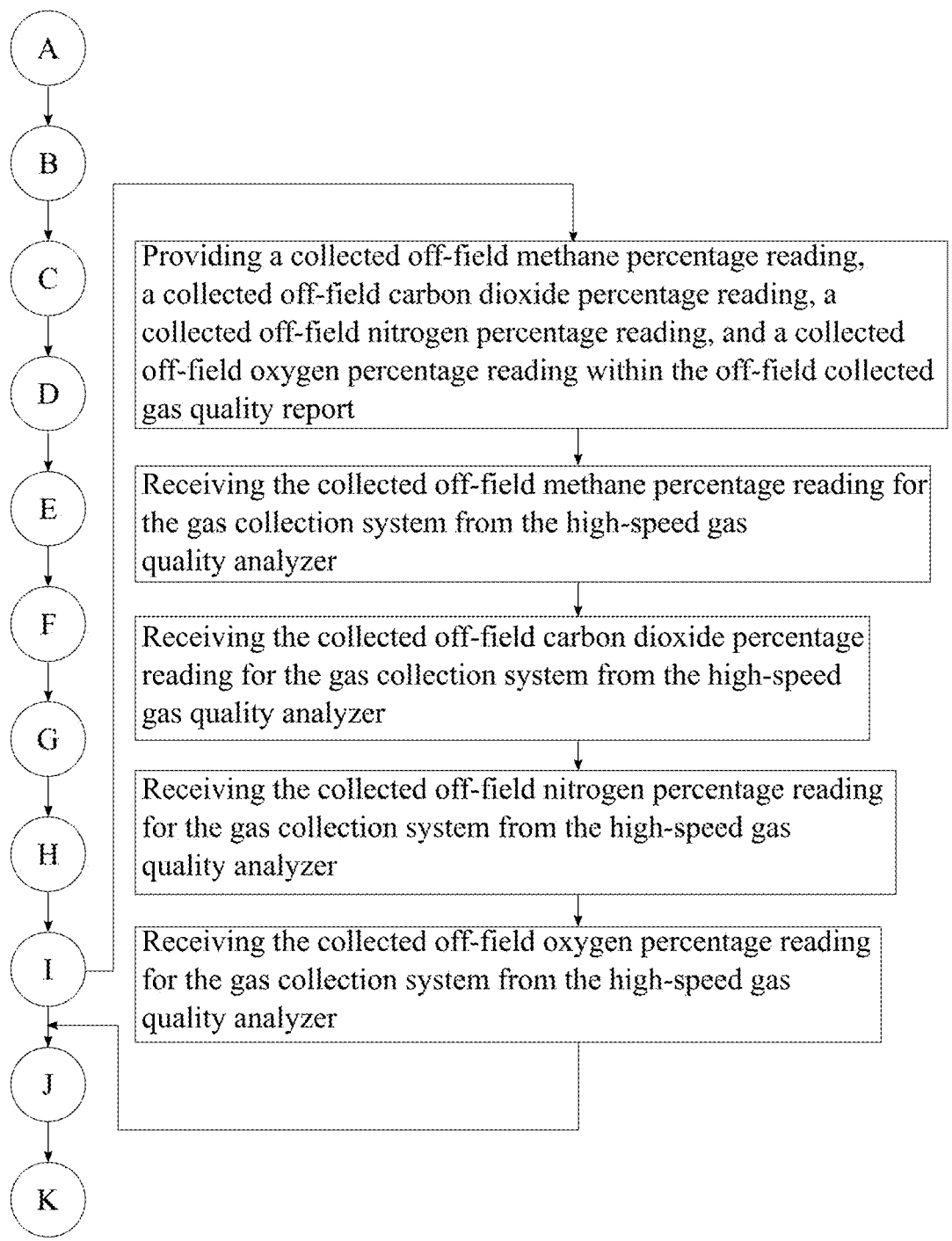
FIG. 7 is a flow chart for the generating the off-field collected gas quality report within the overall method of the present invention.

In reference to FIG. 2 and FIG. 7, the present invention then receives an off-field collected gas quality report for the gas collection system. More specifically, the plurality of collection gas testers that is collected from the gas collection system is processed through a high-speed gas quality analyzer so that the present invention is able to attain an accurate gas quality report in comparison to the gas quality report received from the field-grade landfill gas analyzer. The off-field collected gas quality report includes a collected off-field methane percentage reading, a collected off-field carbon dioxide percentage reading, a collected off-field nitrogen percentage reading, and a collected off-field oxygen percentage reading as each one of those readings represents an overall output of the landfill gas within the present invention. More specifically, when the plurality of collection gas testers is processed through the high-speed gas quality analyzer, the present invention is able to receive the extracted off-field methane percentage reading for the gas collection system, the extracted off-field carbon dioxide percentage reading for the gas collection system, the extracted off-field nitrogen percentage reading the gas collection system, and the extracted off-field oxygen percentage reading the gas collection system.

Figure 8:
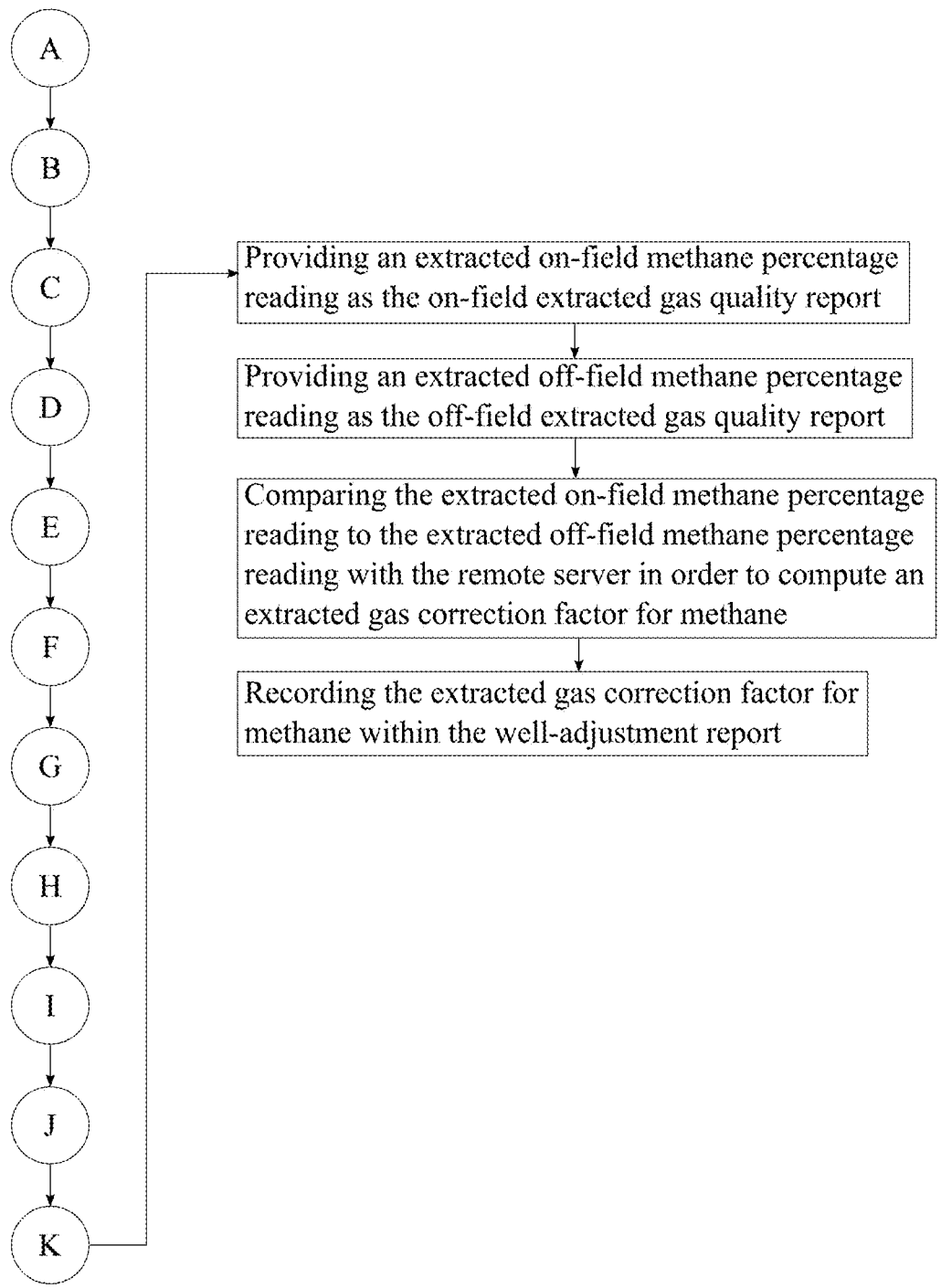
FIG. 8 is a flow chart for calculating the extracted gas correction factor for methane within the overall method of the present invention.

In reference to FIG. 2, the present invention uploads the on-field collected gas quality report and the off-field collected gas quality report to the remote server from the In reference to FIG. 8, the present invention compares the extracted on-field methane percentage reading to the extracted off-field methane percentage reading with the remote server thus computing an extracted gas correction factor for methane. Then, the extracted gas correction factor for methane is recorded within the well-adjustment report so that the field-grade landfill gas analyzer can be recalibrated with the extracted gas correction factor for methane to provide an accurate reading for future iterations.

Figure 9:
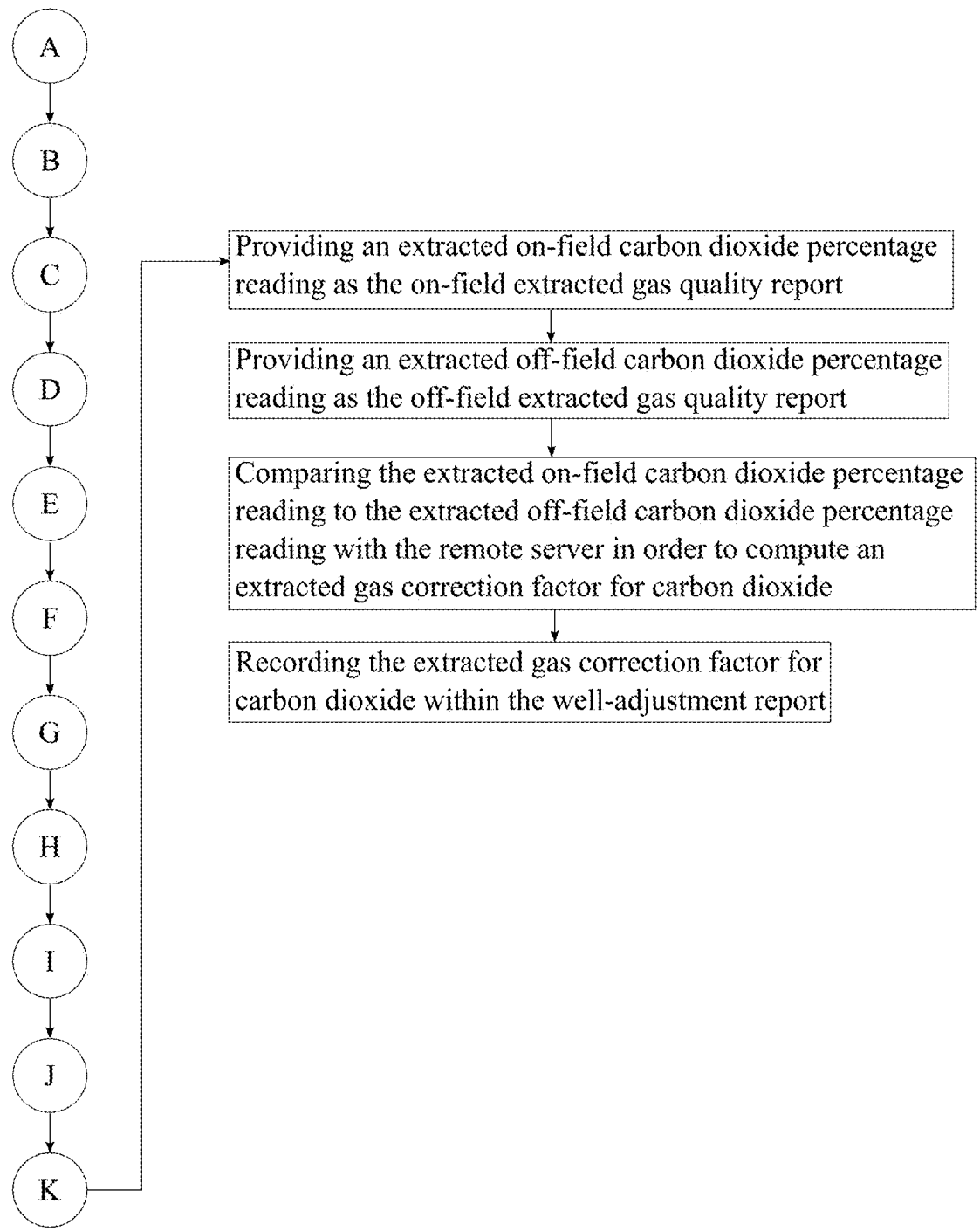
FIG. 9 is a flow chart for calculating the extracted gas correction factor for carbon dioxide within the overall method of the present invention.

In reference to FIG. 9, the present invention compares the extracted on-field carbon dioxide percentage reading to the extracted off-field carbon dioxide percentage reading with the remote server thus computing an extracted gas correction factor for carbon dioxide. Then, the extracted gas correction factor for carbon dioxide is recorded within the well-adjustment report so that the field-grade landfill gas analyzer can be recalibrated with the extracted gas correction factor for carbon dioxide to provide an accurate reading for future iterations.

Figure 10:
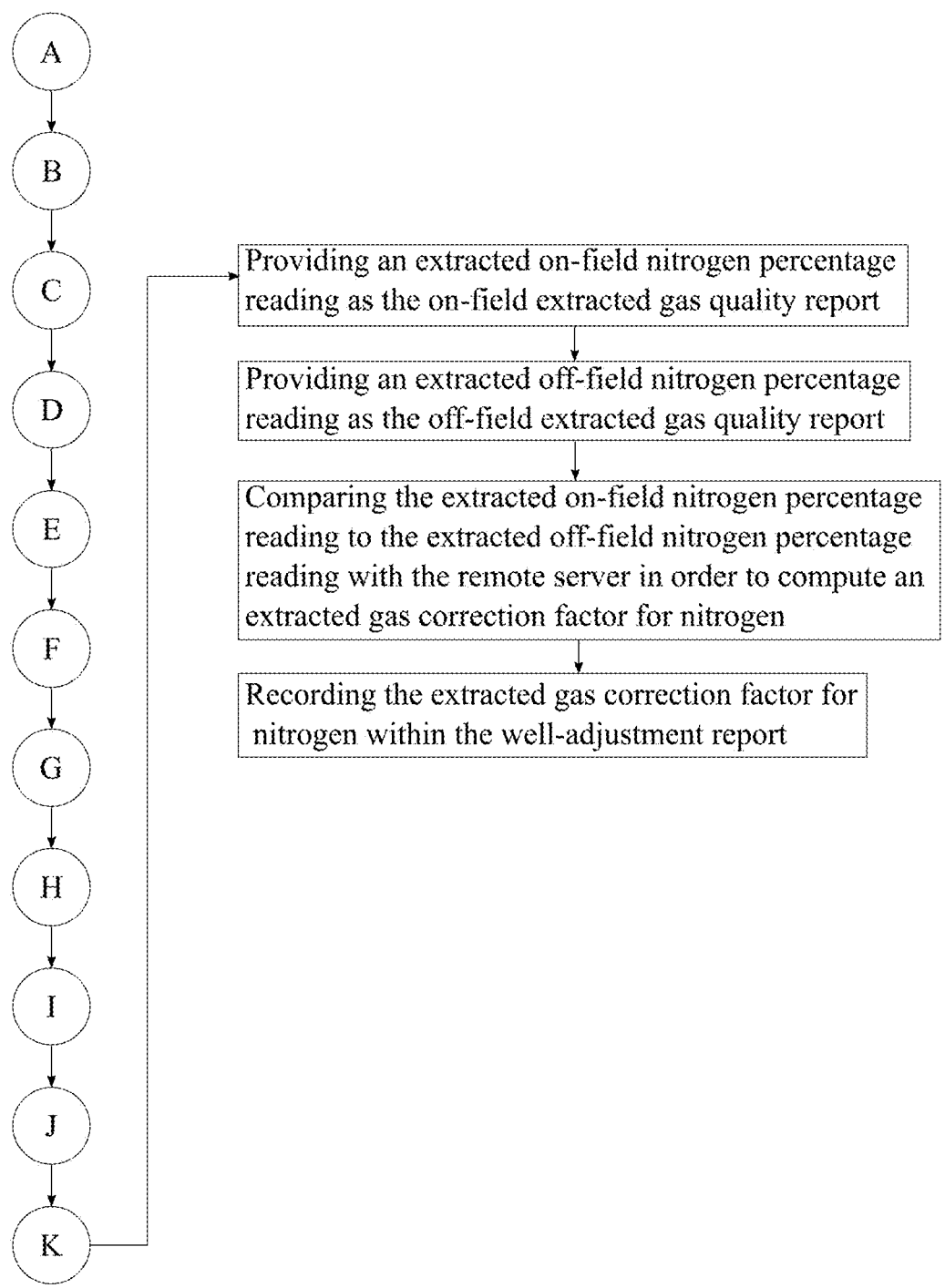
FIG. 10 is a flow chart for calculating the extracted gas correction factor for nitrogen within the overall method of the present invention.

In reference to FIG. 10, the present invention compares the extracted on-field nitrogen percentage reading to the extracted off-field nitrogen percentage reading with the remote server thus computing an extracted gas correction factor for nitrogen. Then, the extracted gas correction factor for nitrogen is recorded within the well-adjustment report so that the field-grade landfill gas analyzer can be recalibrated with the extracted gas correction factor for nitrogen to provide an accurate reading for future iterations.

Figure 11:
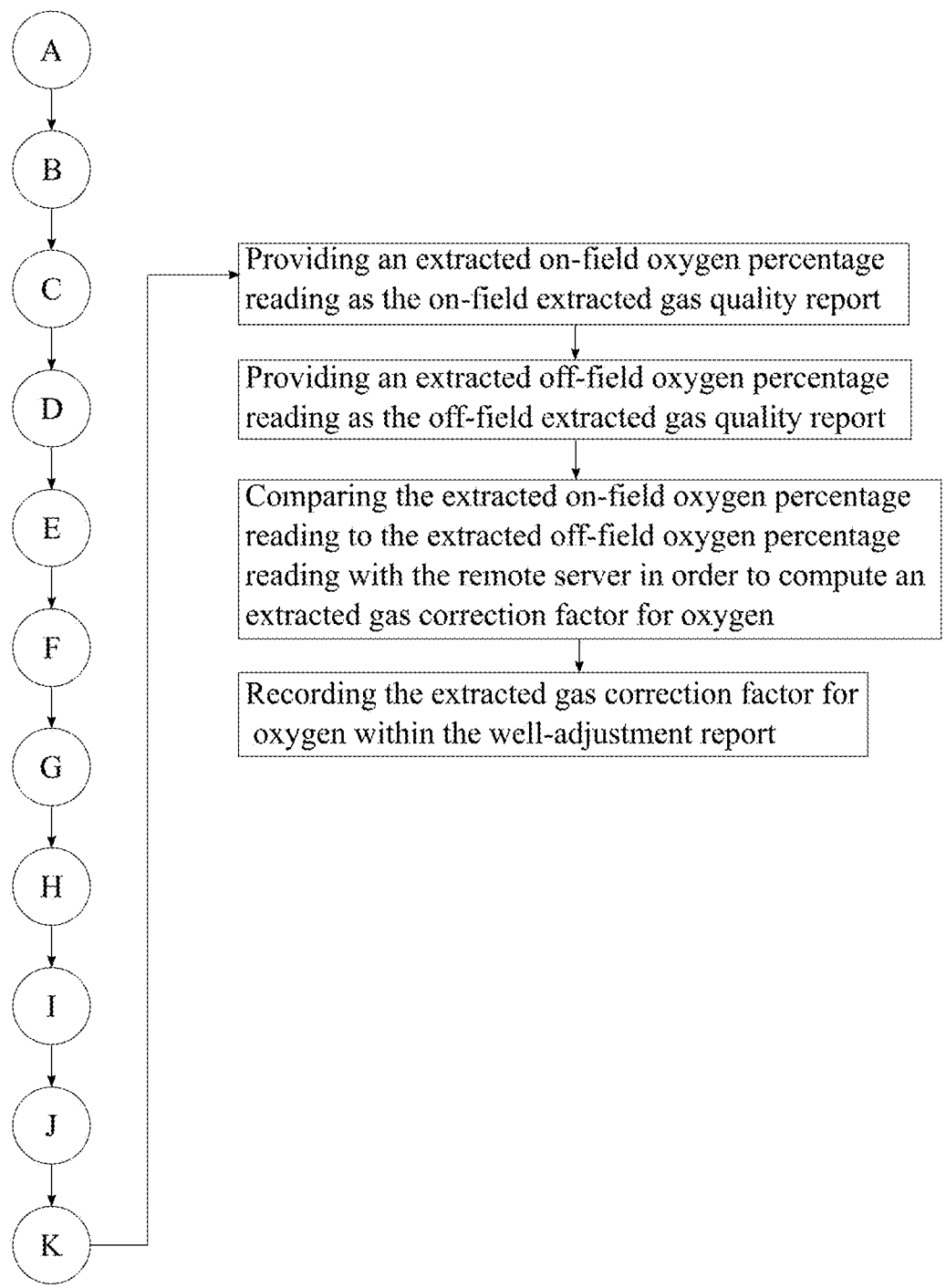
FIG. 11 is a flow chart for calculating the extracted gas correction factor for oxygen within the overall method of the present invention.

In reference to FIG. 11, the present invention compares the extracted on-field oxygen percentage reading to the extracted off-field oxygen percentage reading with the remote server thus computing an extracted gas correction factor for oxygen. Then, the extracted gas correction factor for oxygen is recorded within the well-adjustment report so that the field-grade landfill gas analyzer can be recalibrated with the extracted gas correction factor for oxygen to provide an accurate reading for future iterations.

Figure 12:
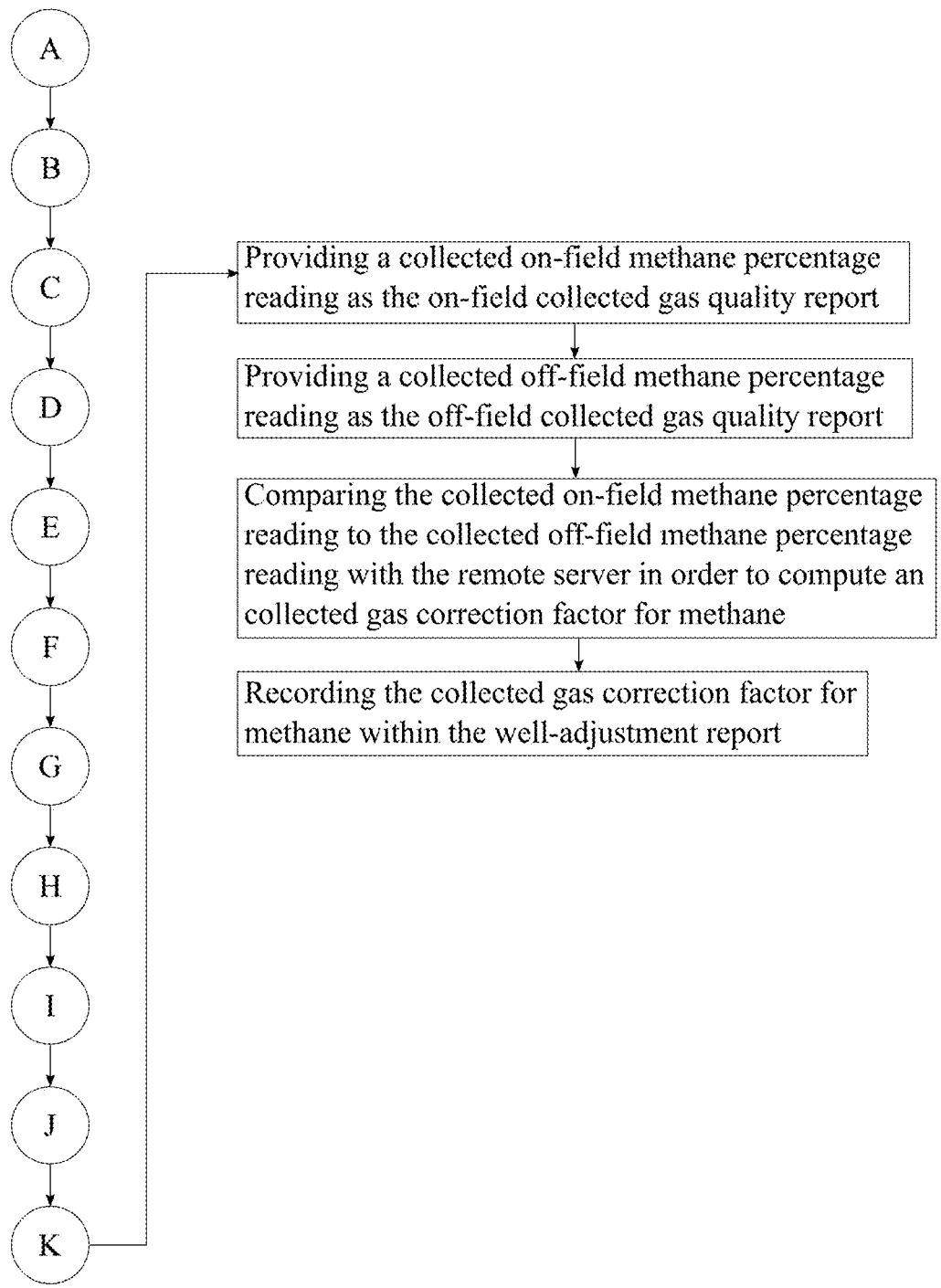
FIG. 12 is a flow chart for calculating the collected gas correction factor for methane within the overall method of the present invention.

In reference to FIG. 12, the present invention compares the collected on-field methane percentage reading to the collected off-field methane percentage reading with the remote server thus computing a collected gas correction factor for methane. Then, the collected gas correction factor for methane is recorded within the well-adjustment report so that the field-grade landfill gas analyzer can be recalibrated with the collected gas correction factor for methane to provide an accurate reading for future iterations.

Figure 13:
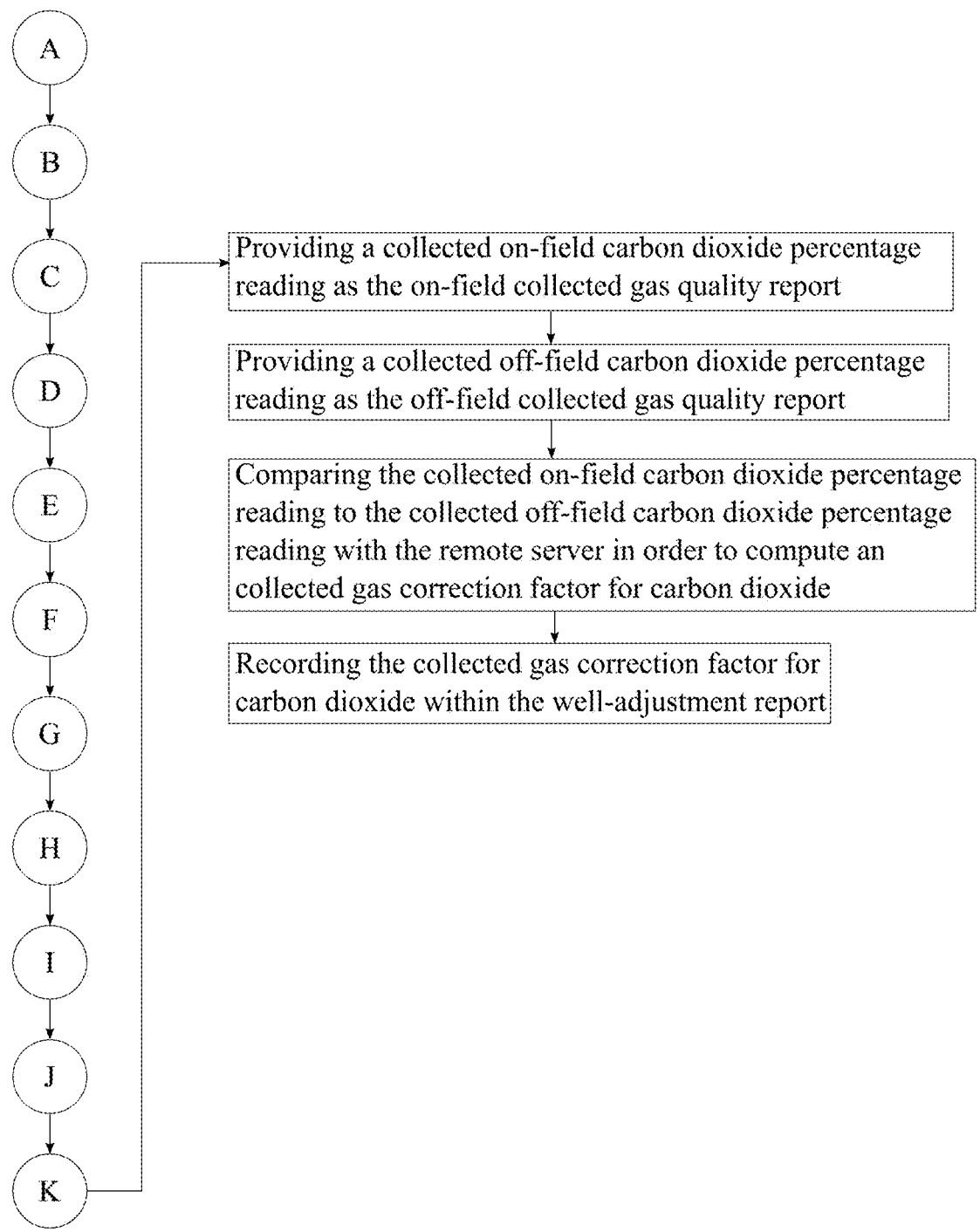
FIG. 13 is a flow chart for calculating the collected gas correction factor for carbon dioxide within the overall method of the present invention.

In reference to FIG. 13, the present invention compares the collected on-field carbon dioxide percentage reading to the collected off-field carbon dioxide percentage reading with the remote server thus computing a collected gas correction factor for carbon dioxide. Then, the collected gas correction factor for carbon dioxide is recorded within the well-adjustment report so that the field-grade landfill gas analyzer can be recalibrated with the collected gas correction factor for carbon dioxide to provide an accurate reading for future iterations.

Figure 14:
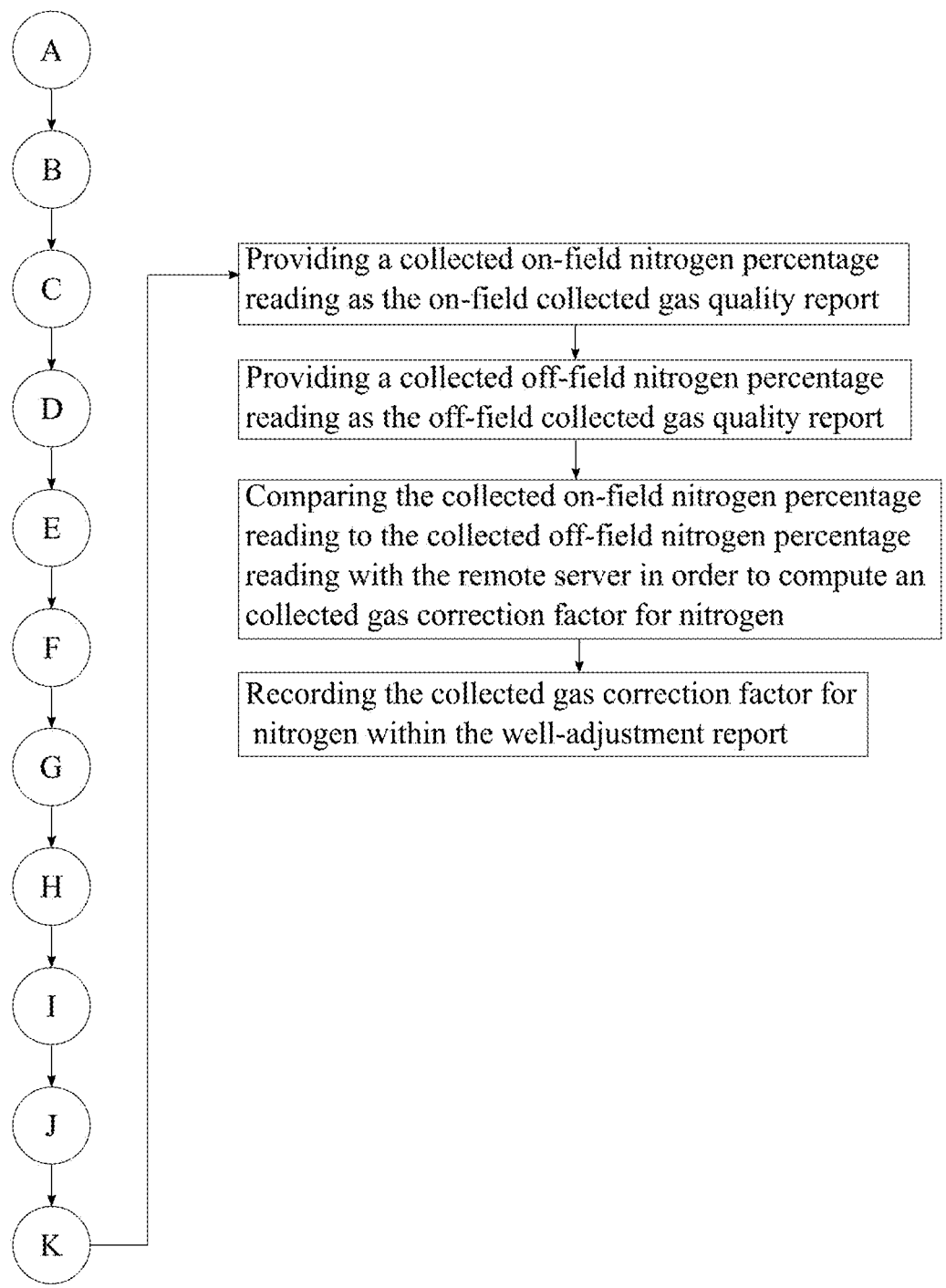
FIG. 14 is a flow chart for calculating the collected gas correction factor for nitrogen within the overall method of the present invention.

In reference to FIG. 14, the present invention compares the collected on-field nitrogen percentage reading to the collected off-field nitrogen percentage reading with the remote server thus computing a collected gas correction factor for nitrogen. Then, the collected gas correction factor for nitrogen is recorded within the well-adjustment report so that the field-grade landfill gas analyzer can be recalibrated with the collected gas correction factor for nitrogen to provide an accurate reading for future iterations.

Figure 15:
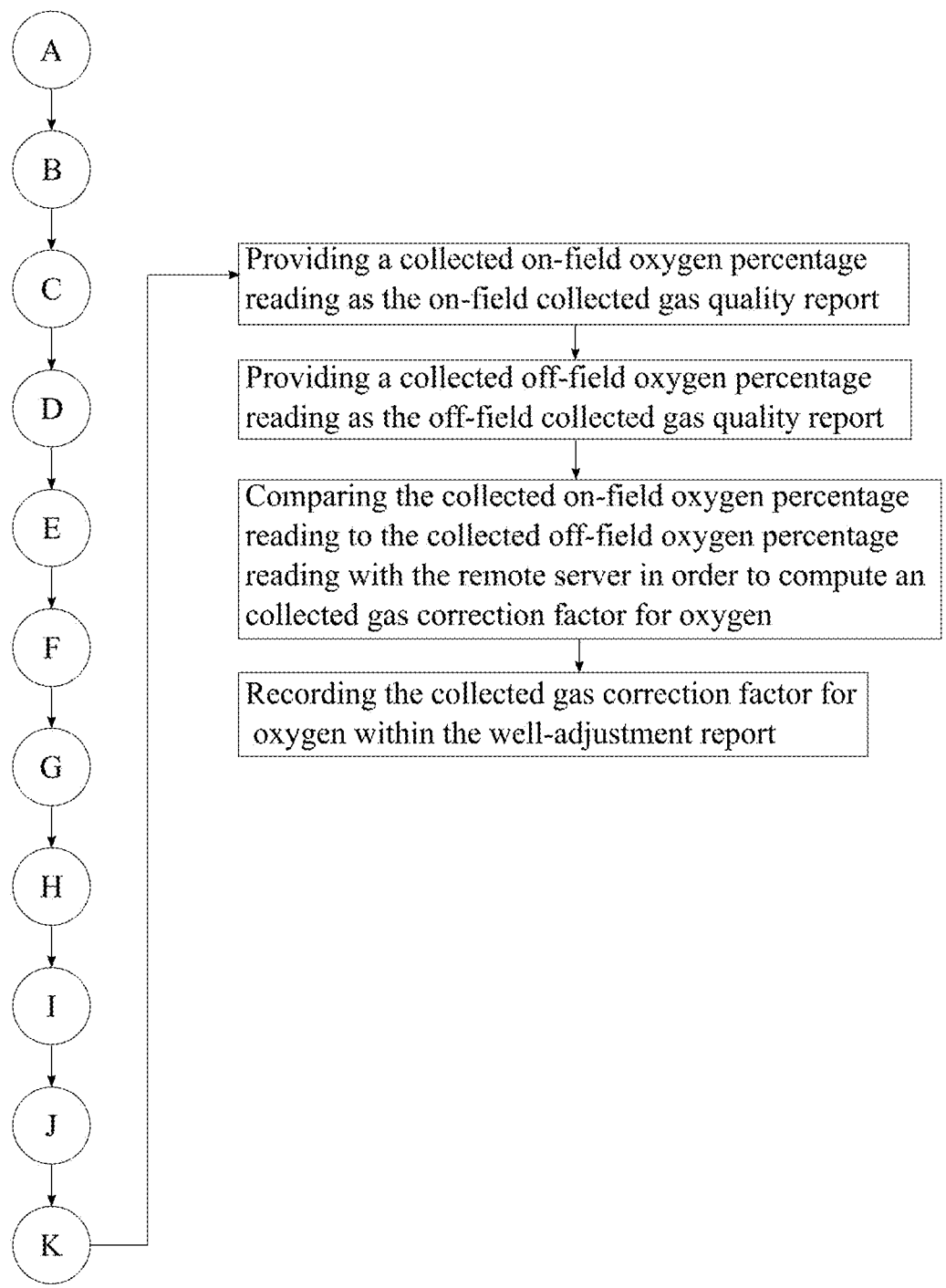
FIG. 15 is a flow chart for calculating the collected gas correction factor for oxygen within the overall method of the present invention.

In reference to FIG. 15, the present invention compares the collected on-field oxygen percentage reading to the collected off-field oxygen percentage reading with the remote server thus computing a collected gas correction factor for oxygen. Then, the collected gas correction factor for oxygen is recorded within the well-adjustment report so that the field-grade landfill gas analyzer can be recalibrated with the collected gas correction factor for oxygen to provide an accurate reading for future iterations.

Figure 16:
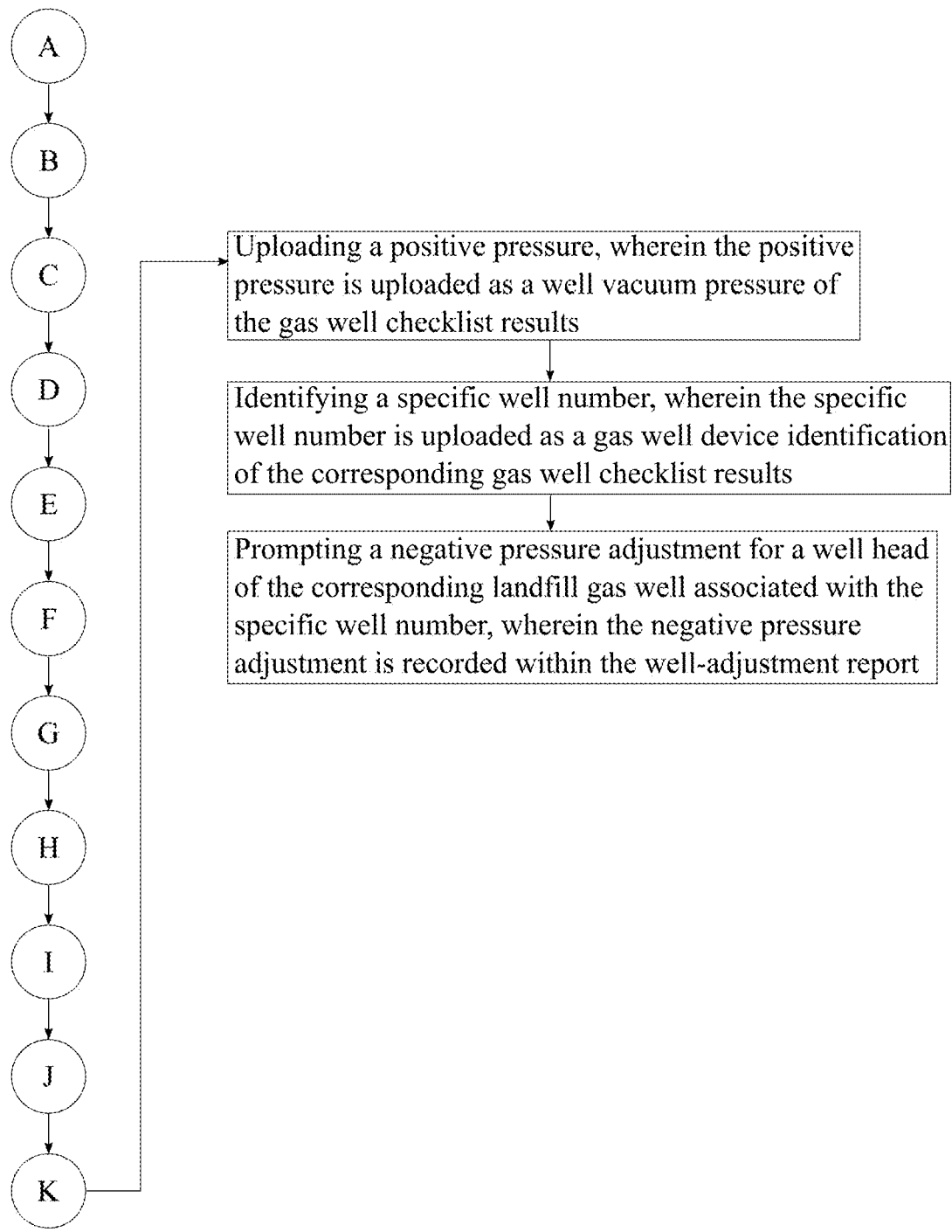
FIG. 16 is a flow chart for calculating the negative pressure adjustment within the overall method of the present invention.
Figure 22:
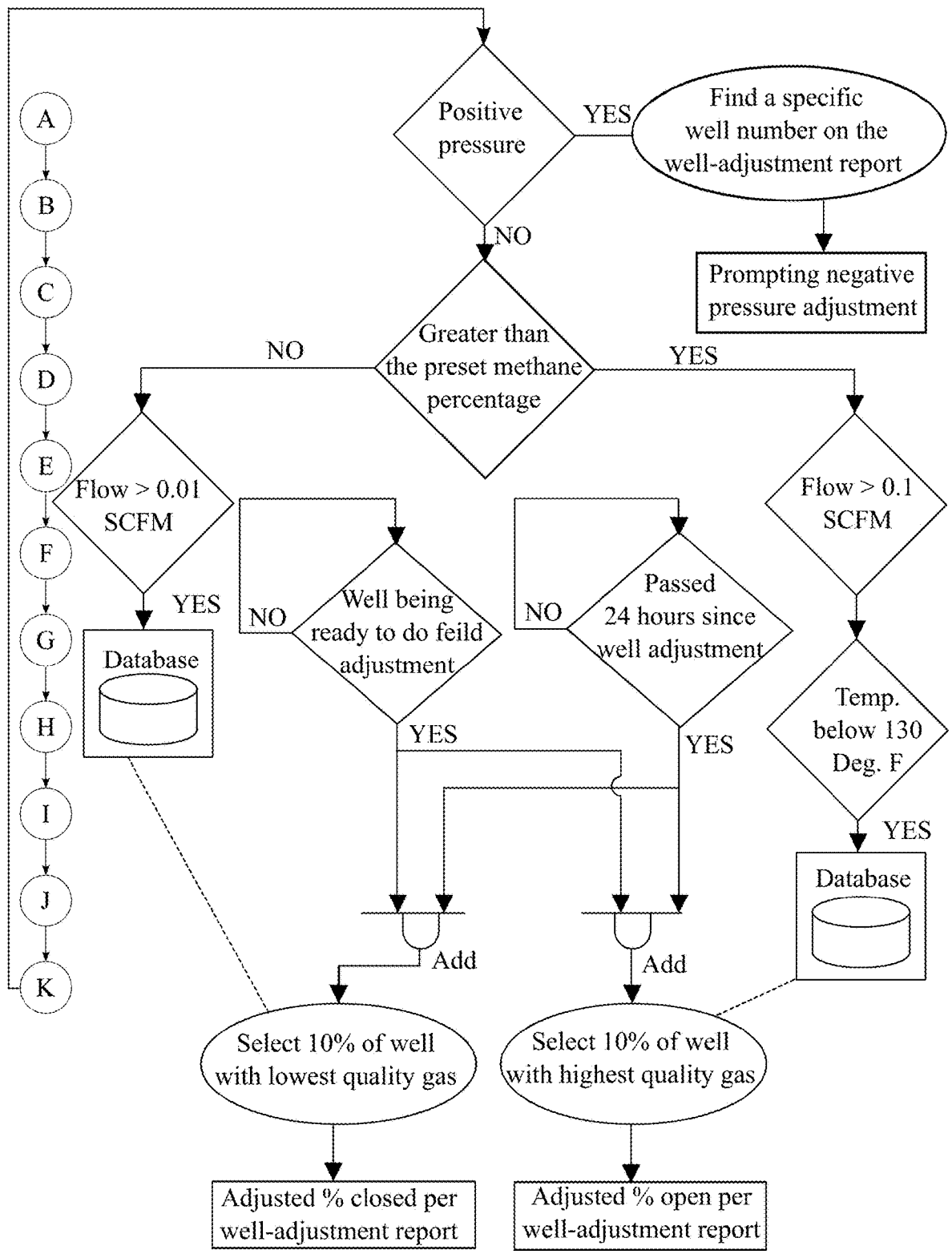
FIG. 22 is a flow chart illustrating basic decision-making process of the present invention within the overall method of the present invention.

In reference to FIG. 16 and FIG. 22, when a positive pressure is uploaded to the remote server as the well vacuum pressure of the gas well checklist results, the present invention first identifies a specific well number that is uploaded as the gas well device identification of the corresponding gas well checklist results. Then, the present invention prompts a negative pressure adjustment for a well head of the corresponding landfill gas well that is associated with the specific well number. Since the negative pressure adjustment is identified by the remote server, the remote server records the negative pressure adjustment within the well-adjustment report. Additionally, the remote server also isolates the well vacuum pressure as the source of problem in order to reduce the number of troubleshooting steps.

Figure 17:
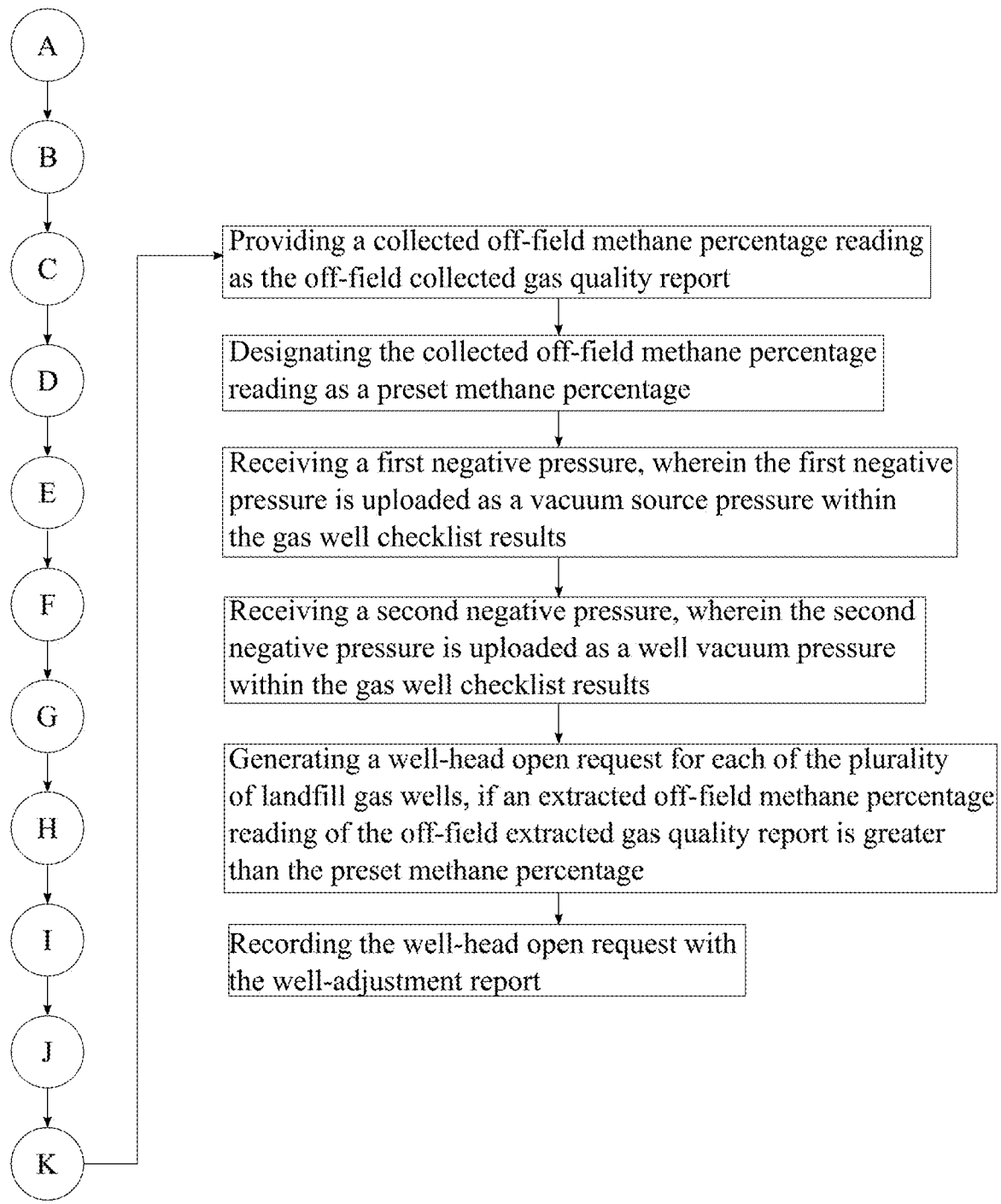
FIG. 17 is a flow chart for calculating the well-head open request within the overall method of the present invention.
Figure 18:
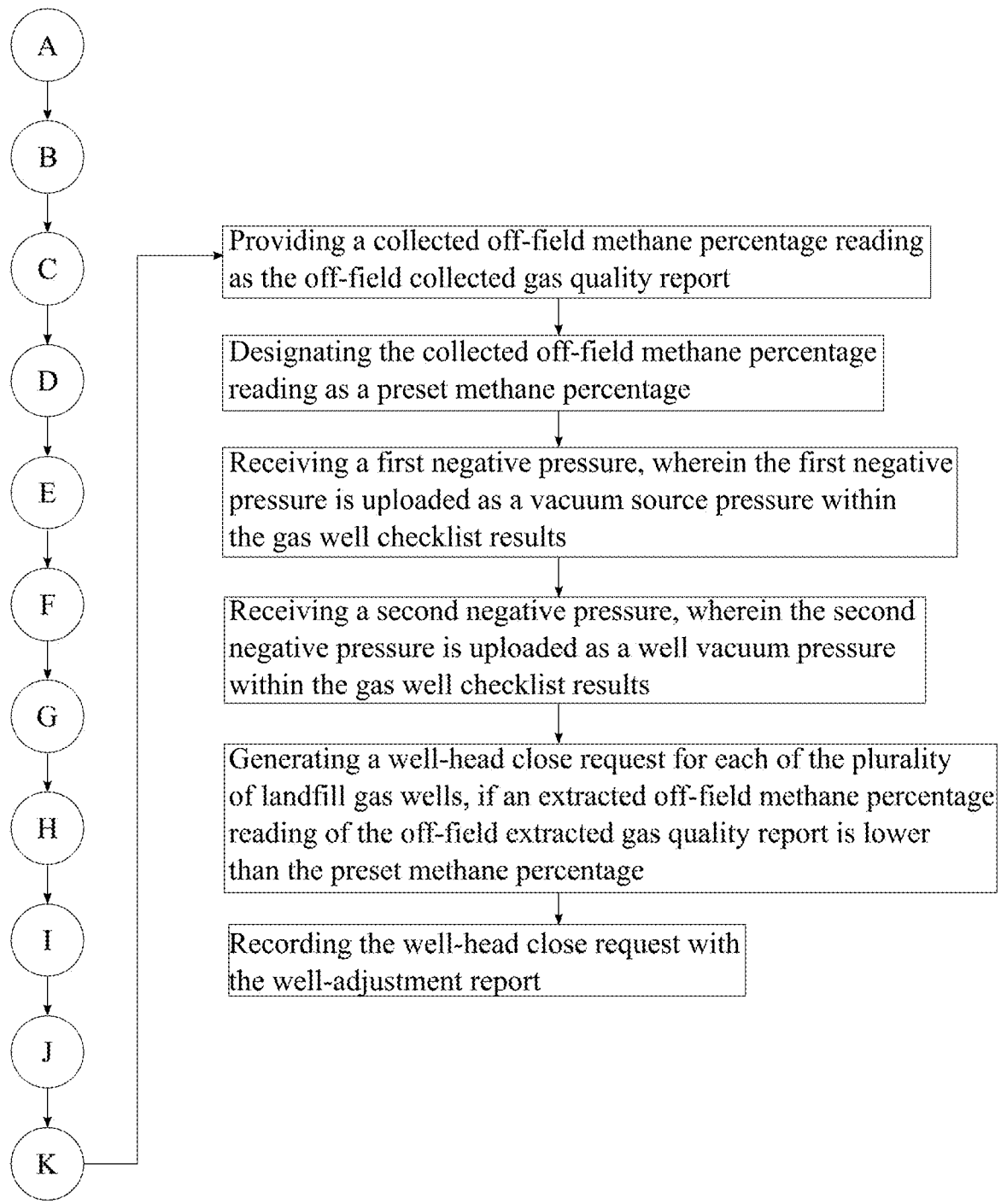
FIG. 18 is a flow chart for calculating the well-head close request within the overall method of the present invention.

In reference to FIG. 17-18 and FIG. 22, the remote server designates the collected off-field methane percentage reading as a preset methane percentage within the present invention so that an average methane output for the plurality of landfill gas wells can be attain. When a first negative pressure is uploaded as the vacuum source pressure and a second negative pressure is uploaded as a well vacuum pressure within the gas well checklist results, the present invention identifies that the plurality of landfill gas wells is in negative pressure. The present invention then generates a well-head open request for each of the plurality of landfill gas wells, if an extracted off-field methane percentage reading of the off-field extracted gas quality report is greater than the preset methane percentage. The well-head open request is then recorded within the well-adjustment report. However, the present invention generates a well-head close request for each of the plurality of landfill gas wells, if an extracted off-field methane percentage reading of the off-field extracted gas quality report is lower than the preset methane percentage. The well-head close request is then recorded within the well-adjustment report.

Figure 19:
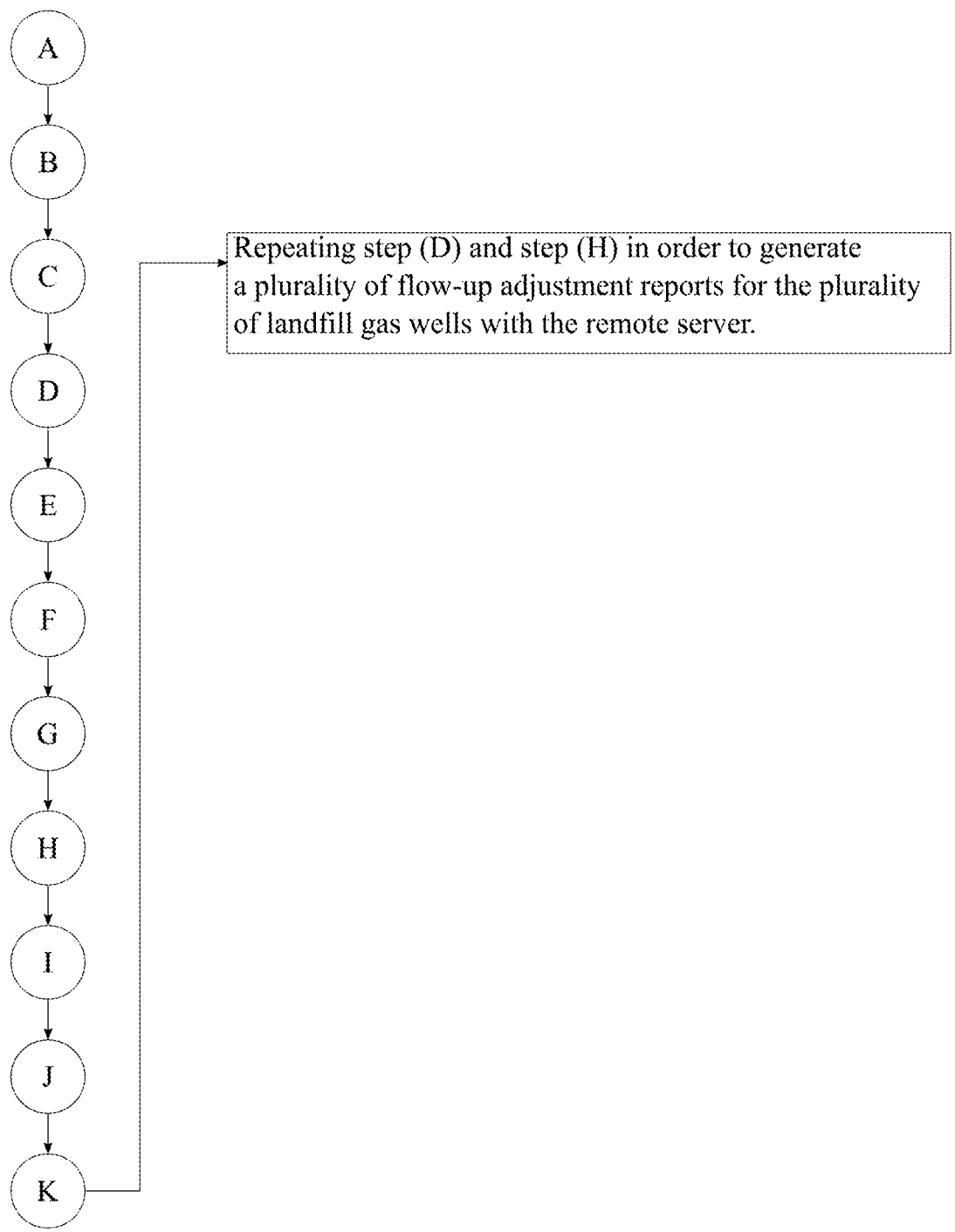
FIG. 19 is a flow chart for calculating the plurality of flow-up adjustment within the overall method of the present invention.

In reference to FIG. 19, once the preliminary adjustments are undertaken within the plurality of landfill gas wells, the present invention initiates a plurality of flow-up adjustment reports. More specifically, the present invention periodically receives the on-field extracted gas quality report for each of the plurality of landfill gas wells and the on-field collected gas quality report for the gas collection system with field-grade landfill gas analyzer so that the remote server is able to generates the plurality of flow-up adjustment reports that efficiently optimize the overall output of the landfill gas. Utilizing data collected the gas well checklist results, the on-field extracted gas quality report, the off-field extracted gas quality report, the on-field collected gas quality report, and the off-field collected gas quality report, a landfill well profile map of hydrogen sulfide can be generated through the present invention. Depending upon the capacity of the measuring device, the present invention utilizes the on-field extracted gas quality report and the on-field collected gas quality report or the off-field extracted gas quality report and the off-field collected gas quality report.

Figure 20:
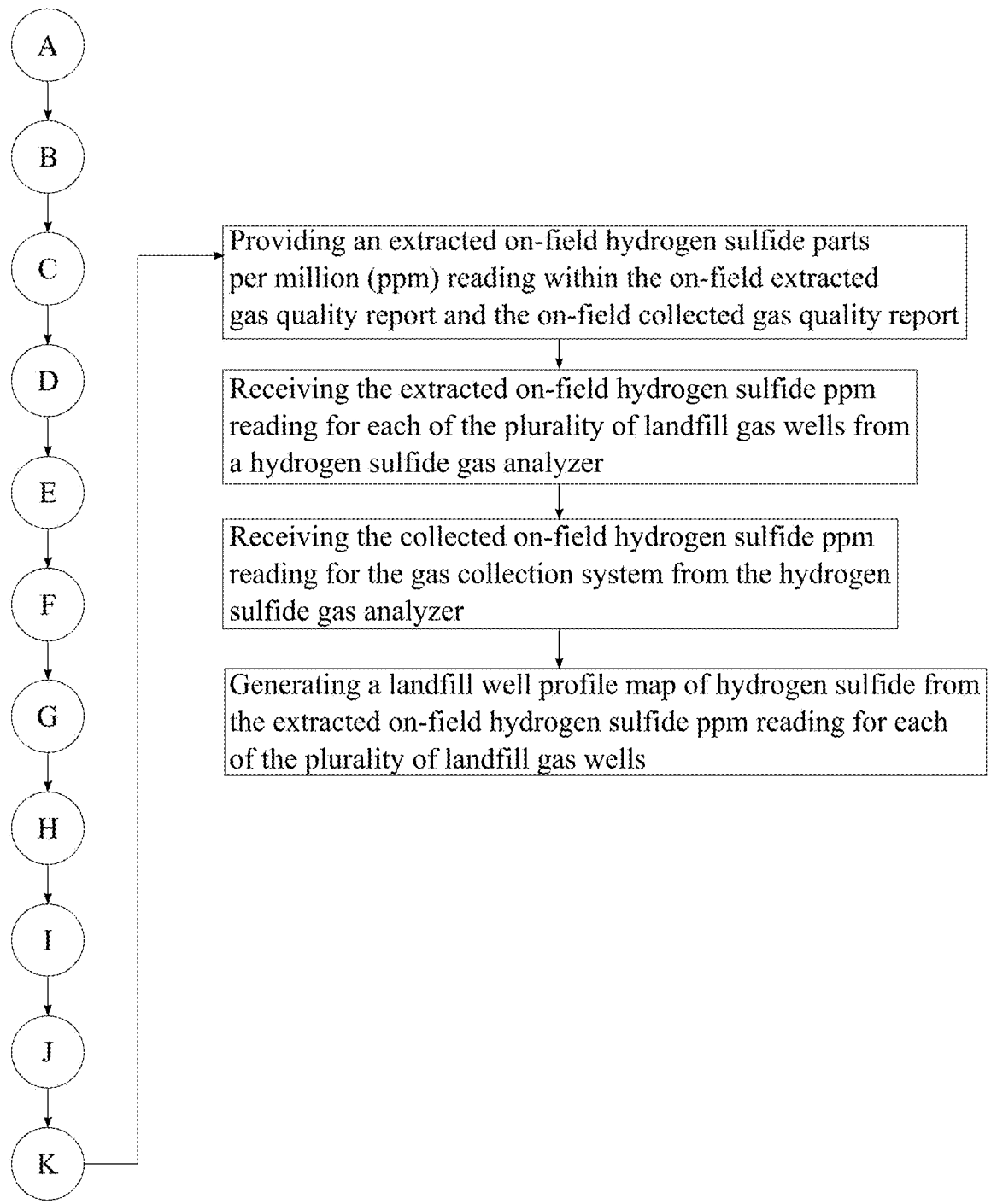
FIG. 20 is a flow chart for generating the profile map from the on-field extracted gas quality report and the on-field collected gas quality report within the overall method of the present invention.
Figure 21:
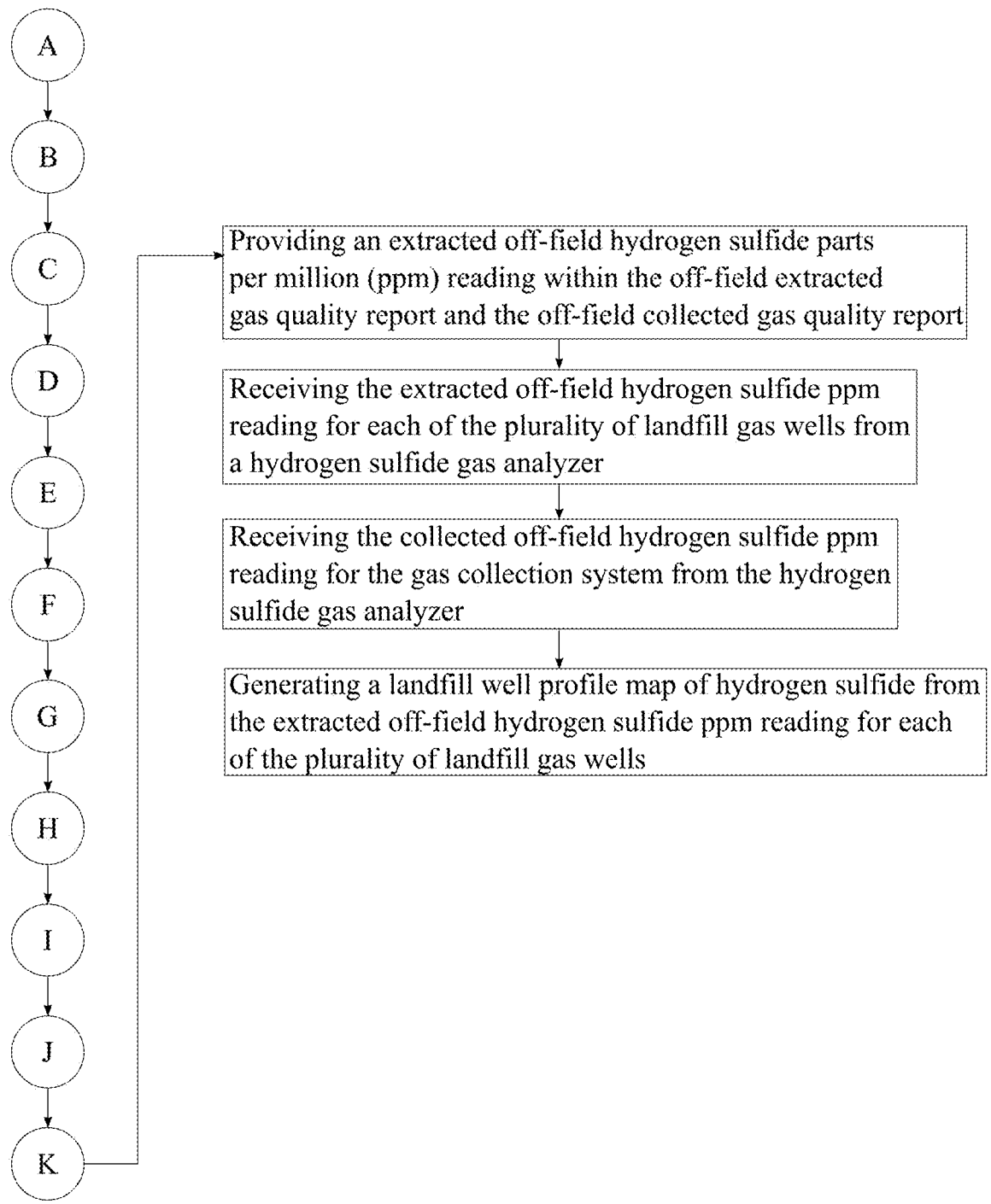
FIG. 21 is a flow chart for generating the profile map from the off-field extracted gas quality report and the off-field collected gas quality report within the overall method of the present invention.
Figure 26:
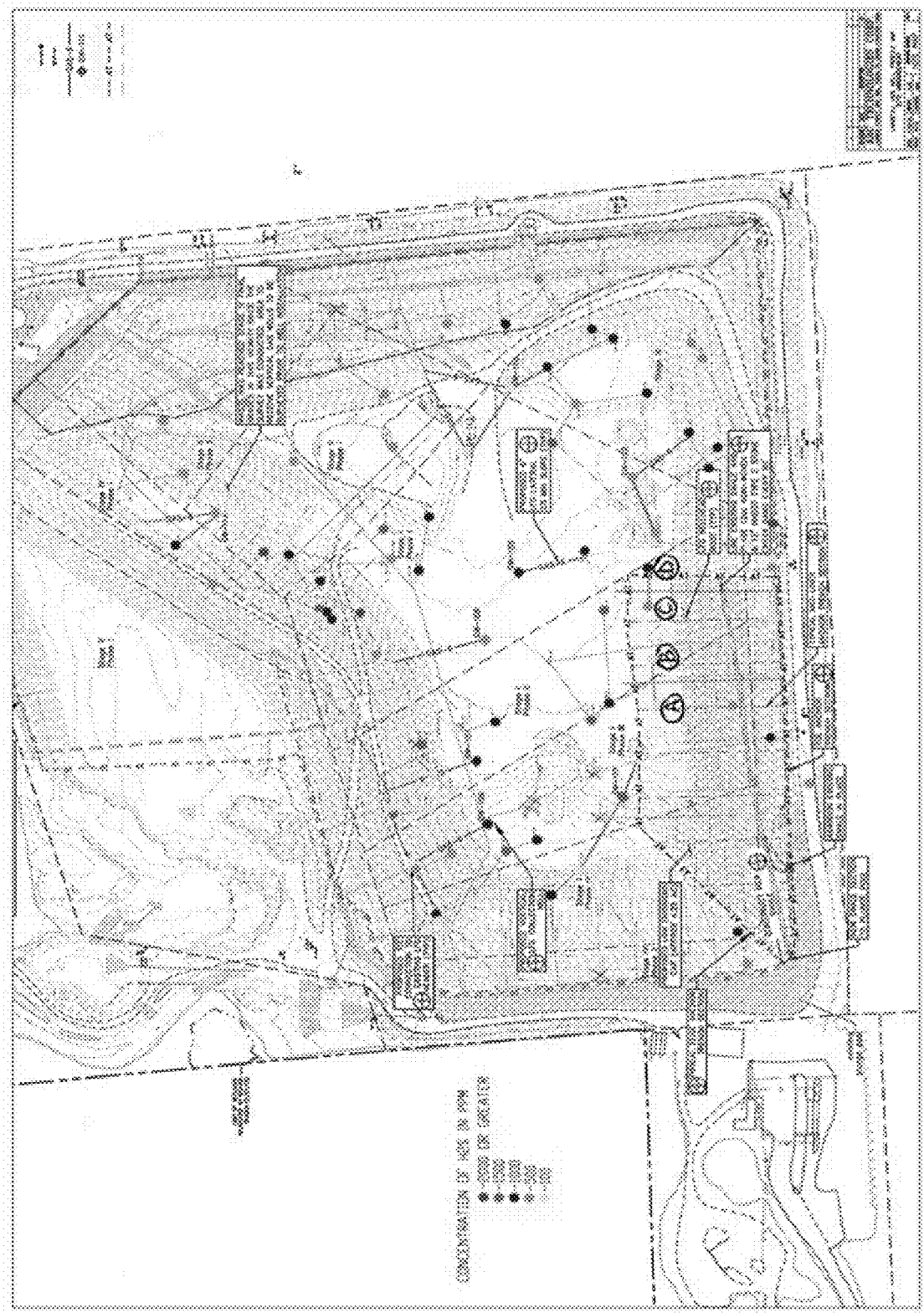
FIG. 26 is a diagram showing the generated landfill well profile map of hydrogen sulfide by the present invention.

In reference to FIG. 20-21, the present invention is able to receive an extracted on-field hydrogen sulfide parts per million (ppm) reading from a hydrogen sulfide gas analyzer so that the extracted on-field hydrogen sulfide parts per million (ppm) reading can be provided within the on-field extracted gas quality report and the on-field collected gas quality report. More specifically, the present invention first receives the extracted on-field hydrogen sulfide ppm reading for each of the plurality of landfill gas wells and the collected on-field hydrogen sulfide ppm reading for the gas collection system from the hydrogen sulfide gas analyzer. The present invention then generates the landfill well profile map of hydrogen sulfide by utilizing only the extracted on-field hydrogen sulfide ppm reading for each of the plurality of landfill gas wells. Optionally, once the present invention receives the extracted off-field hydrogen sulfide ppm reading for each of the plurality of landfill gas wells and the collected off-field hydrogen sulfide ppm reading for the gas collection system from the hydrogen sulfide gas analyzer, the present invention can generate the landfill well profile map of hydrogen sulfide by utilizing only the extracted off-field hydrogen sulfide ppm reading for each of the plurality of landfill gas wells as shown in FIG. 26.

The value of the landfill well profile map of hydrogen sulfide and of each of the collected data enable a landfill well gas sampling technician to understand the future effects that water levels and a more anaerobic environment may have on future hydrogen sulfide production. The landfill well gas sampling technician may also be better prepared to understand and deal with the following issues:

1. Water effects in certain areas of the landfill
2. Turning high hydrogen sulfide production wells to be in overall hydrogen sulfide and sulfur oxide compliance
3. Sizing hydrogen sulfide pretreatment systems for the existing flare 4. Sizing hydrogen sulfide treatment systems for future landfill beneficial projects
5. Forecasting future hydrogen sulfide/methane production Exemplary Case Study Section 1: Executing Summary The following report shows the advantages of using a controlled analytical approach for testing and training to improve the quality of the landfill gas at a specific landfill.

The specific landfill Analysis Proposal was given to Casella Waste Systems, Inc, the owners of the landfill, to confirm the feasibility of enhancing their landfill gas quality for beneficial use as a renewable fuel or RNG (renewable natural gas).

Existing landfill gas upgrade technologies refine landfill gas to meet pipeline quality and CNG gas, but are limited by the amount of air that is contained in the raw landfill gas. Air migration into landfill gas collection systems is the number one issue that prevents more than 75% of all landfills from being candidates for a beneficial use renewable fuel project.

This report further details the gas value enhancement for the owner regarding increased revenue, environmental benefits and public relations.

The controlled analytical approach and protocol used was developed by ARC Technologies Corporation, having more than twenty years' experience converting landfill gas to high quality pipeline and CNG renewable fuels.

Section 2: Introduction

Prior to the commencement of the testing the specific landfill, it was viewed by the ARC Technologies' team as a viable candidate for a beneficial use renewable fuel project. Past experiences have shown that a landfill with >1500 scfm of landfill gas flow could be qualified as a candidate for a beneficial use project by reducing the air intrusion into the landfill gas collection system. For gas plant capital cost reasons, a target of a maximum of 4% AIR (N2+O2) content of the raw landfill gas is desirable. Once this targeted number of 4% is achieved and maintained the landfill's renewable energy value will increase, allowing ARC's proven technology to be installed on site at the most optimum design basis.

Testing began on June 20 with the help of Eric Fisher (NEOGas North America), three Casella Waste Systems employees and ARC's two-man team using the prepared testing protocol and equipment. ARC's mobile Lab contained the following analytical equipment:

Ametek mass spectrometer with all calibration gases
Qty of 170—H2S 0-2000 ppm Draeger test tubes with test fixture The plan involved testing more than 150 gas wells, condensate traps and cleanouts during the first three days on site. The morning of day four was spent reviewing collected data, summarizing status of the landfill and selecting candidate well heads that should be adjusted to demonstrate an overall reduction of air into the gas collection system. About 20-25 wells were selected to be closed ¼ turn and another 20-25 were selected to be opened ¼ turn. Three well heads also where chosen to be closed ½ turn because of high air content with great gas flow. Fourteen wells showed no flow and no gas sample was taken (readings would have been meaningless).

Day five was spent training and evaluating the test results which showed improvement. The remainder of this document gives the results of the team's efforts.

Section 3: Testing Overview

Field Sampling—The 32-ft. mobile office/lab was equipped with a high accuracy Mass Spectrometer, automated H2S Draeger tube reader and a computer data base logging system. Three sampling test teams were assembled; each team brought from the field a minimum of 20 samples. By the end of the third day all wells, condensate traps and clean-outs were sampled. A sample was also taken before and after all well sampling trips at the discharge of the landfill blower before the landfill flare.

During the well sampling trips, the testing team performed a check of each well head and recorded their findings on the well head check list form. This form had the following check points (the use of the words "well head" also includes clean-outs and condensate traps):

Gas Wells Device ID
Wellhead Type
Vacuum source at well in −WC
Vacuum on well in −WC
Delta P across orifice in WC
H2s in PPM (parts per million)
% CH4
% CO2
% N2
% O2
well head vacuum hose—Good—Fair—Poor—
Was all hardware secured? YES or NO
Was Leak found—YES or NO
Was Leaks Fixed—Temporary YES or NO
Was Leaks Fixed—Permanent YES or NO 0—gives the raw data results of all wells tested during the three-day test period.

Section 4: Continuing Tuning the Landfill

The landfill technician has demonstrated their ability in understanding ARC's approach in reducing air intrusion into the gas collection system. They also understand that compliance comes first regarding their efforts on the landfill. The landfill technician's reporting of the gas quality is evidence of his capability and his strong motivation to do a good job. To date the landfill technician has reported a reduction from over 16% N2 to less than 4% (from 16.4% to 3.8% N2 Mass Spec equivalent or from 12.1% to 2.8% N2 GEM reading) which will be sustainable.

The landfill technician holds the key which enables the landfill owners to increase the value of their gas assets. Management of the landfill should take pride in the landfill technician and encourage their growth that will migrate to all the landfills they hold.

The Software Tool for Continuous Landfill Tuning:

On testing day 5 the landfill technician was given two formatted Excel spreadsheets that converted his GEM readings into equivalent Mass Spec readings for CH4, CO2, N2 and O2 using correction factors. The first sheet was used to record landfill gas quality data readings summarized at the landfill flare. A second sheet was use by the landfill technician to record continuous individual well head gas tuning data.

During the continuing landfill gas quality readings/tuning period, samples were taken using the on-site GEM which is used by the site for compliance reasons. A Mass Spec equivalent reading is needed by the testing team to evaluate gas quality for pipeline and CNG grade equivalent knowing that there are differences between the GEM and the Mass Spec. (GEM reading to Mass Spec equivalent) gives the simple math relationship between the GEM reading to Mass Spec equivalent and the resulting correction factors that are used to obtain Mass Spec equivalent.

Figure 23:
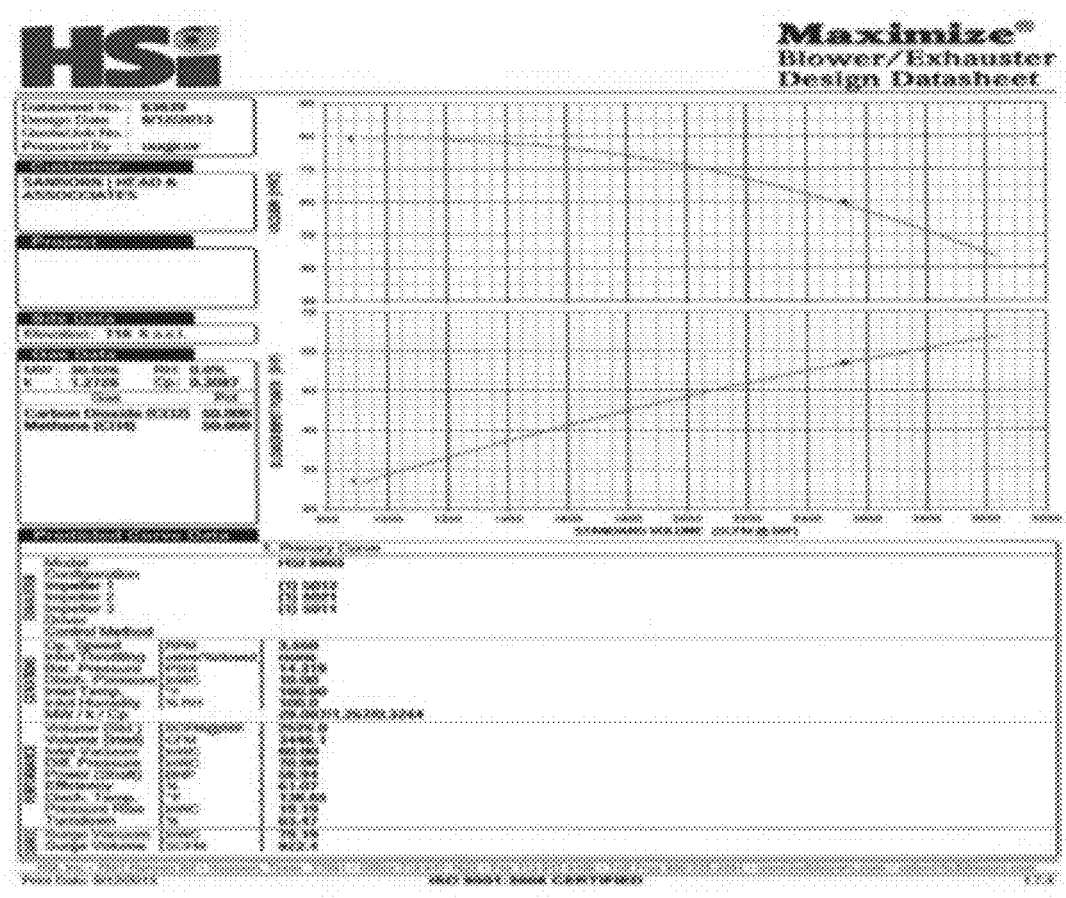
FIG. 23 is a diagram showing the performance primary curve of the blower motor within the system of the present invention.
Figure 24:
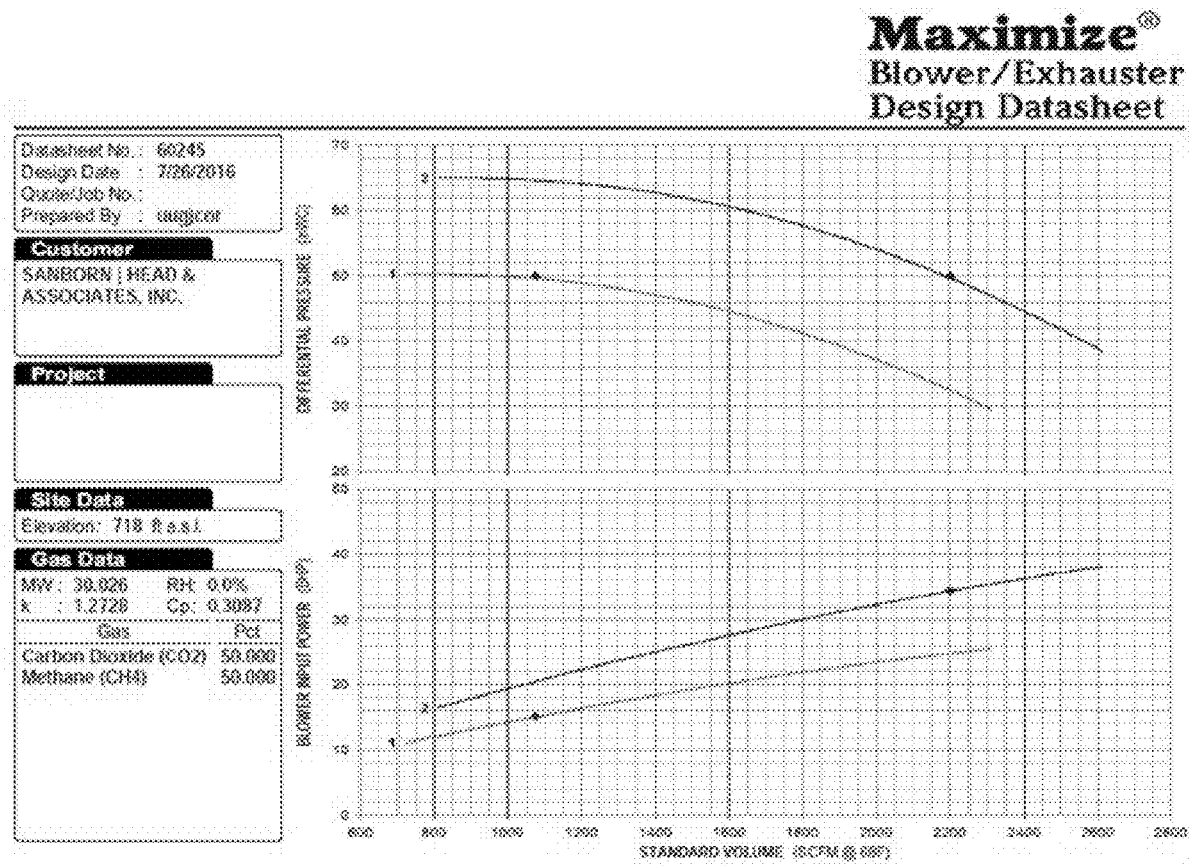
FIG. 24 is a diagram showing the performance primary and auto speed curve of the blower motor within the system of the present invention.

The following reasons dictate that all gas quality data be translated into Mass Spec equivalent:
- GEM's assumes N2 as balance
- GEM's Cal gas tolerances
- GEM is used as a standard for compliance reasons only
- GEM will not qualify as a gas custody measurement device Section 5: Discussion of Resulting Data in Reference to FIG. 23-25

The Predominately Anaerobic Landfill:

In a predominately anaerobic landfill there is an absence of gaseous oxygen meaning that gaseous oxygen is prevented from entering the gas collection system (the system is sealed tight). This type of landfill without high H2S should produce a gas mixture with the following content:
- ~60% CH4
- ~39% CO2
- CH4/CO2 Ratio=1.5:1
- ~1.3% N2
- <0.11% O2
- N2/O2 Ratio=13:1

It should be noted that the high N2/O2 Ratio of 13:1 is a result of O2 being used-up in the bio-mass through aerobic respiration and the N2 remains high regarding the N2/O2 Ratio. This type of leftover N2 is called residual N2 which entered the landfill with the O2 that got reduced through aerobic respiration.

TABLE 1

Flare station gas samples taken from a predominately anaerobic landfill in BC, Canada

| CO2 | N2 | O2 | CH4 |
|---|---|---|---|
| 39.57 | 1.32 | 0.12 | 58.97 |
| 38.46 | 1.34 | 0.11 | 60.08 |
| 39.47 | 1.34 | 0.12 | 59.05 |

One should understand that there will always be aerobic microorganisms in a predominately anaerobic landfill. The key to keeping the landfill predominately anaerobic is to keep the air from reaching the buried bio-mass.

A Landfill with More Aerobic Activity:

In a landfill with more aerobic activity, the aerobic microorganisms access free, gaseous oxygen directly from leaks in the landfill through the active work area, through uncapped areas, broken well casings, broken lines or anywhere that air gets pulled down into the bio-mass. The aerobic process does not generate methane, which accounts for the CH4/CO2 Ratio imbalance.

Aerobic organism's growth is much faster than anaerobes because aerobic respiration is more efficient at generating energy than anaerobic respiration. Again, like predominately anaerobic landfills, aerobic landfills will also contain anaerobic microorganisms that produce methane.

In an aerobic environment increases in carbon dioxide and water will occur along with heat due to the oxidization of the bio-mass into carbon dioxide and water. Assuming no leaks in the gas collection system, this type of landfill without high H2S should produce a gas mixture with the following content,

TABLE 2

~44% CH4
~40% CO2
CH4/CO2 Ratio = 1.1:1
~15% N2
<0.2% O2
N2/O2 Ratio = 15:1

Like a predominately anaerobic landfill, a landfill with more aerobic activity generates a high N2/O2 Ratio as shown above but the percentages of residual N2 are much larger (15% versus 1.3%).

A landfill with high aerobic activity would not be a desirable candidate for a High BTU gas project because of high capital equipment cost to reduce the nitrogen. Again, understanding how and why air is being pulled into the bio-mass could lead to a corrective solution that may or may not be cost effective.

The Reality of all Landfills:

There are no perfect landfills regarding being only anaerobic in nature to produce methane. All landfills contain aerobic microorganisms which continually reproduce using free gaseous oxygen directly from the landfill and other oxygen sources (landfill organic materials or by decomposition of inorganic material in the waste).

With this said, parts of a landfill could be classified as more aerobic than other parts of a landfill. The same as anaerobic sections of a landfill which will promote methanogenic bacteria that produce methane. To understanding this in relation to a specific landfill it is necessary to adjust (tune) each of the well heads in order to provide a predominantly anaerobic methane production from the landfill.

Knowing that one section of the landfill is more aerobic (even one well) we should try to understand why the section is indeed more aerobic. In most cases it is because we are pulling too hard on the well regarding vacuum and there is a nearby air opening/problem. We must look at each landfill section and associated wells so as to understand the problems better and if the problems can be fixed, we must fix them. If a problem cannot be fixed, we should make a long-term plan and pull more softly with the vacuum at that point (while still staying in compliance).

The Specific Landfill:

On Jun. 20, 2016 the specific landfill was landfill gas quality tested at the inlet of the flare's blower. The following are the results of the data collected:

TABLE 3

| Date & time | Test sample and location | Flare Vacuum recorded | Flare's Flow Meter Flow | CH4 % | CO2 % | N2 % | O2 % | Testing instrumentation |
|---|---|---|---|---|---|---|---|---|
| Jun. 20th 10 am | Test sample #1 taken from vacuum side of | −35.5 to 38.5" WC | '2625 SCFM | 45.19 | 35.82 | 16.25 | 2.55 | O2, N2, CH4 & CO2 tested with Ametek mass spectrometer |

TABLE 3-continued

| Date & time | Test sample and location | Flare Vacuum recorded | Flare's Flow Meter Flow | CH4 % | CO2 % | N2 % | O2 % | Testing instrumentation |
|---|---|---|---|---|---|---|---|---|
| Jun. 20th 10 am | Test sample #2 taken from vacuum side of flare's blower | −35.5 to 38.5" WC | `2625 SCFM | 39.8 | 32.28 | 23.82 | 4.28 | O2, N2, CH4 & CO2 tested with Ametek mass spectrometer |
| Jun. 20th 10 am | Test sample #3 taken from vacuum side of flare's blower | −35.5 to 38.5" WC | `2625 SCFM | 46.8 | 36.45 | 14.4 | 2.2 | O2, N2, CH4 & CO2 tested with Ametek mass spectrometer |
| Jun. 20th 10 am | Test sample #4 taken from vacuum side of flare's blower | −35.5 to 38.5" WC | `2625 SCFM | 46.9 | 35.56 | 14.2 | 2.14 | O2, N2, CH4 & CO2 tested with Ametek mass spectrometer |

Each of the four samples taken at that time was sampled from a static line/tube on the suction side of the flare's blower. ARC's sampling syringes needed to purge the underground static line/tube which was not completely confirmed. Sample #2 above shows that air was falsely introduced into the sample.

A plan was devised to remove this air intrusion by adding a sample port downstream of the blower at the flare's flame arrester. During a short lunch break, ARC acquired the needed pipe fitting for a new pressure sample port at the flare. Sample #4 was taken that confirmed the following:

TABLE 4

| Date & time | Test sample and location | Flare Vacuum recorded | Flare's Flow Meter Flow | CH4 % | CO2 % | N2 % | O2 % | Testing instrumentation |
|---|---|---|---|---|---|---|---|---|
| Jun. 20th 2:15 pm | Test sample #5 taken from pressure side of flare's blower | −35.5 to 38.5" WC | `2625 SCFM | 45.8 | 37.4 | 14.8 | 1.9 | O2, N2, CH4 & CO2 tested with Ametek mass spectrometer |

The test team agreed that future samples would be taken in the morning to establish the landfill's gas quality. Note that the test team agreed that no well heads would be adjusted until agreed by the team on day 4 (after completing all well sampling). On the morning of day 2 (June 21) the flowing samples and results were recorded:

TABLE 5

| Date & time | Test sample and location | Flare Vacuum recorded | Flare's Flow Meter Flow | CH4 % | CO2 % | N2 % | O2 % | Testing instrumentation |
|---|---|---|---|---|---|---|---|---|
| Jun. 21st 9:30 am | Test sample #6 taken from pressure side of flare's blower | −35.5 to 38.5" WC | `2625 SCFM | 44.9 | 38.8 | 14.0 | 2.32 | O2, N2, CH4 & CO2 tested with Ametek mass spectrometer |

TABLE 5-continued

| Date & time | Test sample and location | Flare Vacuum recorded | Flare's Flow Meter Flow | CH4 % | CO2 % | N2 % | O2 % | Testing instrumentation |
|---|---|---|---|---|---|---|---|---|
| Jun. 21$^{st}$ 9:30 am | Test sample #7 taken from pressure side of flare's blower | −35.5 to 38.5" WC | `2625 SCFM | 43.9 | 38.1 | 15.2 | 2.67 | O2, N2, CH4 & CO tested with Ametek mass spectrometer |

For the starting gas quality benchmark, we will use the average of the two above samples:

TABLE 6

| Average CH4 % | Average CO2 % | Average N2 % | Average O2 % |
|---|---|---|---|
| 44.4 | 38.45 | 14.6 | 2.5 |

Using this starting gas quality landfill benchmark, we can analyze the nature of the landfill regarding being either predominately aerobic or predominately anaerobic. First, we see that O2 is high at 2.5% which mainly comes from air leaks in the gas collection system. Second, the ratio of N2/O2 is equal to 5.84:1 telling us that very little O2 is being used up underground by aerobic activity. Further insuring us that we have air leaking into the gas collection system (meaning that this is not the result of air being pulled down into the biomass); we must factor this air out of our aerobic/anaerobic calculation.

At this point in our testing program residual N2% can be calculated but due to the large quantity of air leaks still in the system it has no real meaning regarding our goal of qualifying the landfill for a High BTU plant.

Progress—On July 5 the test team got an update from the landfill technician at the specific landfill. He reported—"MS adjusted numbers after 4 days of no system manipulation are: CH4—50.2, CO2—38.8, N2—6.1, O2—1.2. H2S=700." At this point in time the O2 was down lower than half of what it was at our starting benchmark but still was extremely high for a predominately anaerobic landfill. The N2/O2 ratio now equals 5.1:1, down from 5.84:1, meaning that there is still air being pulled into the gas collection system. Knowing at this point that all major above ground air leaks have been fixed, the remaining leaks must be coming from air being pulling in near the cap of the landfill or being pulling from wells that are near openings in the landfill (around well heads, pea gravel areas, trenches, condensate/J traps or anywhere else that air can find its way in). It should be noted that the specific landfill will likely not reach a complete anaerobic status with N2/O2 ratio of say 13:1. The gas collection system was not designed to do so and there are other problems in the well/header system. The system only needs to get to a level of 4% AIR and still pull vacuum as hard as needed to prevent emissions and odors on the landfill.

To achieve our goal of less than 4% air on the specific landfill we must understand each gas well regarding what is happening underground. Using the gas quality data generated from the wells we can understand how to tune each well, which in turn will improve the overall gas quality of the landfill's gas asset.

Report ending Progress—On July 25 the landfill technician reported for this final report the following data
Date/time Jul. 25, 2016 7:42
Landfill Vacuum—40" WC
Landfill gas flow 2250 scfm
CH4 55.7% GEM reading
CO2 41.1% GEM reading
2.8% GEM reading
0.4% GEM reading
H2S 700 ppm
51.4668% Mass Spec equivalent
39.27516% Mass Spec equivalent
3.794% Mass Spec equivalent
0.782% Mass Spec equivalent
The July 25 results show that O2 was down again with a N2/O2 ratio equaling 4.85:1 further down from 5.1:1, but still shows room for improvement.

The residual N2% can be calculated at this final reporting point using the following equation:

$F$=Flare's N2/O2 ratio(4.85)

$N$=Normal Air N2/O2(3.76)

$T$=Total Flow to flare(2250 scfm)

RN=Recorded N2 flow to flare gas (scfm)=3.794%*2250 scfm=85.4 scfm

RO=Recorded O2 flow to flare gas (scfm)=0.782%*2250 scfm=17.6 scfm

EO=Expected O2 if no aerobic activity=RN*0.266=22.7 scfm

Residual $N2$=(EO−RO)*$N$=(22.7−17.6)*3.76=19.18 scfm

The above results tell us that 22% of the N2 going to the flare is residual N2 and the remaining N2 is from air leaks other than air passing through the bio-mass. The resulting difference between the total N2 flow to the flare (85.4 scfm) and the residual N2 flow (19.18 scfm) confirms 66.22 scfm of non-residual N2 flow, which is 2.94% of the total flow of N2 to the flare.

This indicates that there is a lot of room for improvement regarding further reducing N2 on this landfill and gives the decision makers a comfort margin when forecasting the success of a capital cost project.

The biggest question has been answered, meaning that the landfill will sustain a high BTU project. the landfill technician's July 25 landfill gas quality report now enables the decision makers to forecast a successful capital cost project.

The second question is: can the landfill technician keep the landfill in a more predominately anaerobic condition? The answer to this is, YES, because within less than a month the landfill technician with his limited resources has enhanced the landfill gas quality as predicted by ARC's testing/training team. ARC sees this as only the beginning phase of improving the landfill gas quality.

Section 6: Discussion of the H2S Results

Using the H2S data collected shown for each landfill gas well, a landfill H2S Well profile map was generated. The map has the following color-coded legend which defines each recorded H2S sample points:

Concentration of H2S in PPM:
Red—2000 or greater
Pink—1500
Blue—1000
Green—500
Yellow—100

Reviewing the map, one needs to use 0 to identify well numbering which also contains coding for well types. Each well type has certain purposes regarding gas and water protection/compliance reasons.

Just like landfill gas quality for N2/O2%, the total sum of each well's H2S in ppm is summarized at the landfill flare inlet. The following examples of a few good anaerobic production wells demonstrate that each well could have a quite different H2S reading.

TABLE 7

| Well # | ppm of H2S |
|---|---|
| GW-73 | 800 |
| GW-77 | 550 |
| GW-79 | 410 |
| GW-85 | 275 |
| GW-86 | 1425 |
| GW-87 | 340 |
| GW-88 | 200 |

Many of these wells are near each other but produce higher or lower concentrations of H2S. Water, higher percentage of construction waste and anaerobic environment (lower gaseous O2 content) promote higher H2S levels. Likewise lack of water, low percentage of construction waste and aerobic environment (higher gaseous O2 content) promote low H2S levels.

For years this landfill had taken in construction waste and used construction waste for cover resulting in an underground environment which creates H2S. Now the landfill owners must deal with this problem.

The intent of this test study is not to solve the H2S problem at the landfill. The value we get from the test study may help us to understand the future effects that water levels and a more anaerobic environment will have on future H2S production.

As we further promote the anaerobic process there will be an increase in methane and H2S production which will not be proportional to each other. Hydrogen sulfide production occurs faster than methane production when wallboard is pulverized allowing more surface area for the bacteria. To forecast the H2S/CH4 production rate would be hard to do and it is not in the scope of this document. Although knowing construction material is no long being taken into the landfill, one could speculate that the existing construction material may show a short-term increase in H2S production because of faster H2S production, but a long-term depletion of the wallboard will eventually allow for lower H2S concentrations.

When sizing a H2S pretreatment process for a potential High BTU plant it is good practice to allow for future/undetermined high H2S levels. The existing recorded 700 ppm levels at the landfill and the variables described in this section dictate that the H2S pretreatment process be sized for at least 1000 ppm of H2S.

Section 7: Discussion of the Total Flow to the Flare

As shown in section 5, the landfill gas flow to the flare was recorded at about 2625 scfm. The flow reading was erratic, ranging from 2500-2750 scfm as well as erratic blower speed/current readings. The fluctuation in the recorded scfm, blower speed and motor current could simply be a matter of tuning the landfill's vacuum process control PID loop.

0 gives the blower motor nameplate information, the factory design blower motor curve and the present running blower motor curve information.

The following factory flare blower motor curve data tells us that the flare/blower/blower motor system design point:

| PERFORMANCE | Volume (Std.) | [SCFM@68 F.] | 2525.0 |
|---|---|---|---|
| | Volume (Inlet) | [CFM] | 3446.1 |
| | Inlet Vacuum | [inWC] | 60.00 |
| | Diff. Pressure | [inWC] | 70.00 |
| | Power (Shaft) | [BHP] | 56.94 |
| | Efficiency | [%] | 61.07 |
| | Disch. Temp. | [° F.] | 136.65 |
| | Pressure Rise | [inWC] | 19.19 |
| | Turndown | [%] | 63.47 |

At the present time, the blower is not running at its design flow and HP. To certify the actual existing flow meter reading we must use the second furnished blower motor flow curve.

Curve number 2 shows the following current running conditions which is used to verify actual landfill gas flow at the flare:

| | Predicted Curve Data | | |
|---|---|---|---|
| | | | .Auto Speed |
| EXHAUSTER | Model | | |
| | Configuration | | |
| | Impeller 1 | | (1) 5012 |
| | Impeller 2 | | (1) 5021 |
| | Impeller 3 | | (1) 5011 |
| | Driver | | |
| | Control Method | | |
| CONDITIONS | Op. Speed | [RPM | 2,963 |
| | Inlet Throttling | [valve/% closed | none |
| | Bar. Pressure | [PSIA | 14.319 |
| | Disch. Pressure | [inWC | 10.00 |
| | Inlet Temp. | [° F. | 100.00 |
| | Inlet Humdity | [% RH | 100.0 |
| | MW/k/Cp | | 29.140/1.267/0.3235 |
| PERFOR-MANCE | Volume (Std.) | [SCFM@68 F. | 2200.0 |
| | Volume (Inlet) | [CFM | 2822.7 |
| | Inlet Vacuum | [inWC | 40.00 |
| | Diff. Pressure | [inWC | 50.00 |
| | Power (Shaft) | [BHP | 34.38 |
| | Efficiency | [% | 60.75 |
| | Disch. Temp. | [° F. | 125.56 |
| | Pressure Rise | [inWC | 14.88 |
| | Turndown | [% | 63.32 |
| SURGE | Surge Pressure | [inWC | 64.88 |
| | Surge Volume | [SCFM | 807.0 |

Knowing that the blower is set to pull about −40" WC of vacuum on the field, with 50" WC differential, at motor RPM speed of about 3000 rpm and the metered motor Hp of about 35 HP, the project's confirmed flow equals about 2200 scfm. This confirms the existing landfill gas flow meter reading with the flow meter reading being 15-20% higher.

Section 8: Conclusions

The following general conclusions can be drawn from this study.

1. The testing/training study demonstrated the use of an analytical well tuning approach to enhance the gas quality at the specific landfill.

2. The study confirmed the actual total landfill gas flow at the specific landfill. This flow confirmation enables the decision makers to forecast a successful capital cost project.

3. The study established that there is a comfortable margin regarding further landfill gas enhancements which further forecasts a successful capital cost project.

4. The study itemized H2S levels in the landfill, described the nature of the H2S problem, described realistic future expectation for H2S generation and established a minimum H2S gas pretreatment size. Correct equipment sizing for H2S treatment will give the decision makers the needed information to detail out the future capital cost project.

Appendices A: Three Day Well Head Testing Results

| Gas Wells | Vacuum source at well in - "WC | Vacuum on well in - "WC | Delta P across orifice in "WC | H2s in PPM | CH4 | CO2 | N2 | O2 | well head vacuum hose - Good-Fair-Poor- | Was all hardware secured? YES or NO | Was Leak found - YES or NO | Was Leaks Fixed - Temporary YES or NO | Was Leaks Fixed - Permanent YES or NO | Notes: |
|---|---|---|---|---|---|---|---|---|---|---|---|---|---|---|
| | | | | | | MASS SPEC READINGS | | | | | | | | |
| GW-3 | -9.9 | -5.5 | 0.8 | 1300 | 57 | 42.6 | 0 | 0.67 | G | Y | N | N/A | N/A | |
| GW-5 | -8.1 | -0.1 | 0.3 | 550 | 55 | 41.2 | 2.3 | 1.3 | G | Y | N | N/A | N/A | |
| GW-8 | -0.8 | 0 | 0.2 | 800 | 52 | 38.3 | 7.2 | 2 | P | Y | N | N/A | N/A | |
| GW-9 | -8.6 | -0.22 | 0.25 | 400 | 47 | 34.7 | 15.9 | 2.4 | F | Y | N | N/A | N/A | |
| GW-16A | -34 | -0.1 | 0 | 200 | 41 | 33.5 | 22.1 | 3 | F | Y | N | N/A | N/A | |
| GW-17A | -17.5 | -1.35 | 0.06 | | 47 | 30.9 | 17.8 | 3.8 | F | Y | N | N/A | N/A | MISSING H2S READING - |
| GW-24 | -13.2 | -0.5 | 0.12 | 950 | 48 | 32.3 | 11.8 | 2.8 | F | Y | N | N/A | N/A | |
| GW-26 | -12.6 | -0.9 | 0.01 | 700 | 51 | 38.1 | 0.32 | 2.1 | F | Y | N | N/A | N/A | |
| GW-29R | -25.5 | -0.7 | 0.1 | 220 | 42 | 31.4 | 23.5 | 2.8 | P | Y | N | N/A | N/A | |
| GW-30 | -20 | -1 | 0 | 325 | 57 | 38.9 | 2.9 | 0.8 | P | Y | N | N/A | N/A | |
| GW-31 | -31.1 | -30.5 | 0 | 700 | 53 | 36.2 | 8.9 | 2 | P | Y | N | N/A | N/A | |
| GW-36 | -13.6 | -3.8 | 0 | 200 | 53 | 41.9 | 3.2 | 0.4 | P | Y | N | N/A | N/A | |
| GW-37R | -23.6 | -0.26 | 0.07 | | NO SAMPLE TAKEN | | | | P | Y | N | N/A | N/A | MISSING H2S READING - |
| GW-39 | -22 | -13.3 | 0 | | 49 | 33.6 | 15.4 | 2.2 | F | Y | N | N/A | N/A | |
| GW-40 | -34 | -18.5 | 0.1 | 1150 | 44 | 33.2 | 18.4 | 3.6 | F | Y | N | N/A | N/A | |
| GW-41 | -14.4 | -2.9 | 0.4 | 620 | 48 | 35.6 | 14.3 | 2.2 | P | Y | N | N/A | N/A | |
| GW-42 | -12.1 | -6.2 | 0.16 | 850 | 46 | 34.6 | 17.4 | 2 | P | Y | N | N/A | N/A | |
| GW-43 | -12.7 | -1.5 | 0.05 | 900 | 48 | 37.3 | 12.7 | 1.4 | P | Y | N | N/A | N/A | |
| GW-44 | -12.8 | -0.7 | 0 | 200 | 57 | 37.8 | 3.1 | 1.1 | P | Y | N | N/A | N/A | |
| GW-46 | -12.5 | -2.8 | 0.08 | 100 | 45 | 35.9 | 17.8 | 1.4 | P | Y | N | N/A | N/A | |
| GW-48 | -20 | -1.74 | 0 | 100 | 45 | 35.9 | 17.8 | 1.4 | P | Y | N | N/A | N/A | |
| GW-49 | -24 | -0.15 | 0 | 210 | 56 | 44 | 0 | 0.5 | F | Y | N | N/A | N/A | |
| GW-51 | -6.8 | -1.9 | 1.7 | 200 | 48 | 40.1 | 10.1 | 1.3 | P | Y | N | N/A | N/A | |
| GW-52 | -8.9 | -1.39 | 0.08 | 375 | 38 | 30.6 | 28.5 | 2.7 | P | Y | N | N/A | N/A | |
| GW-53 | -12.7 | -5.3 | 0.27 | 300 | 45 | 36.3 | 17.6 | 0.63 | P | Y | N | N/A | N/A | |
| GW-54 | -12.5 | 0 | 0 | 2600 | 41 | 35.4 | 20.6 | 2.4 | F | Y | Y | Y | N | |
| GW-55 | -12.5 | -10 | 0.5 | 800 | 54 | 39 | 4 | 0.9 | P | N | Y | Y | N/A | well valve handle not working |
| GW-56 | -13.2 | 0.81 | 1.02 | | NO SAMPLE TAKEN | | | | G | Y | N | N/A | N/A | |
| GW-57 | -11.8 | -10.3 | 2.07 | 200 | 27 | 27.5 | 42.1 | 2.6 | G | Y | N | N/A | N/A | |
| GW-58 | -8.7 | -0.29 | 0.14 | 1400 | 58 | 39.9 | 1.5 | 0.9 | G | Y | N | N/A | N/A | |
| GW-59 | -4 | 0.17 | 0 | 520 | 54 | 37.3 | 6.6 | 1.9 | F | N | Y | Y | N | 4" coupling NEEDS FIXED |
| GW-60 | | | | | | | | | | | | | | |
| GW-61 | -8.5 | -0.22 | 0.23 | 100 | 49 | 38.2 | 10.6 | 1.9 | G | Y | N | | | |
| GW-62 | | | | | | | | | | | | | | |
| GW-63 | -6.6 | -7.6 | 0 | 1300 | 53 | 40.4 | 5.3 | 1.7 | G | Y | N | N/A | N/A | |
| GW-64 | -9 | -8.4 | 0 | 800 | 49 | 41 | 7.9 | 2.2 | G | Y | Y | Y | Y | |
| GW-73 | -8 | -8 | 0 | 800 | 31 | 41.9 | 20.3 | 0.8 | P | Y | N | N/A | N/A | |
| GW-74 | -18.3 | -0.54 | 0.09 | 30 | 53 | 31.8 | 13 | 2.6 | F | Y | N | N/A | N/A | |

-continued

| Device ID | | | | | | | | | | | | | | |
|---|---|---|---|---|---|---|---|---|---|---|---|---|---|---|
| GW-75 | −19.6 | −21 | 0 | 300 | NO SAMPLE TAKEN | | | 1.6 | F | Y | N | N/A | N/A | |
| GW-76 | −34.3 | −0.33 | 0.3 | 550 | 44 | 31.3 | 23.4 | 1.45 | F | Y | N | N/A | N/A | |
| GW-77 | −13.7 | −11.9 | 0.29 | 410 | 50 | 38.5 | 9.6 | 2.9 | P | Y | N | N/A | N/A | |
| GW-79 | −13.7 | −2.8 | 6.9 | 820 | 48 | 37 | 11.9 | 2.4 | P | Y | N | N/A | N/A | |
| GW-81 | −9 | −0.8 | 0 | 1000 | 47 | 37.6 | 12.3 | 2.6 | P | Y | N | N/A | N/A | |
| GW-82 | −10 | 0 | 0.08 | 780 | 48 | 35.2 | 13.9 | 3 | P | Y | N | N/A | N/A | |
| GW-83 | −10 | −0.36 | 0 | 570 | 50 | 35.2 | 12.1 | 1.3 | F | Y | N | N/A | N/A | |
| GW-84 | −20 | −1.5 | 0.05 | 275 | 52 | 38 | 8.6 | 2.1 | P | Y | N | N/A | N/A | |
| GW-85 | −13.5 | −2.38 | 0.17 | 1425 | 48 | 36.2 | 13.5 | 0.7 | F | Y | N | N/A | N/A | |
| GW-86 | −9 | 0.1 | 0.36 | 340 | 52 | 41.5 | 0.6 | 3.2 | P | Y | N | N/A | N/A | |
| GW-87 | −9 | −7.5 | 0.1 | 200 | 48 | 35.8 | 12.9 | 0.9 | F | Y | N | N/A | N/A | |
| GW-88 | −9.1 | −7.1 | 0.27 | 400 | 45 | 39.8 | 14.4 | 0.64 | G | Y | N | N/A | N/A | |
| GW-90 | −0.3 | −0.2 | 0.7 | 100 | 54 | 45.3 | 0 | 1.8 | G | Y | N | N/A | N/A | |
| GW-91 | −0.4 | −0.1 | 0.11 | | 54 | 38 | 6 | | | | | | | NO SOURCE VACUUM AT WELL hose crimped -- replace hose |
| GW-92 | 0 | −0.1 | 0.05 | | NO SAMPLE TAKEN | | | | | | | | | |
| GW-93 | 0 | −2 | 0.05 | 25.0 | 56.9 | 41.0 | 1.6 | 0.4 | P | Y | N | N/A | N/A | |
| GW-94 | −3.5 | −3 | 1 | 100.0 | 54.0 | 37.1 | 8.0 | 0.8 | F | Y | N | N/A | N/A | |
| GW-95 | −3.9 | −0.1 | 0.15 | 900.0 | 51.0 | 37.5 | 10.5 | 0.7 | F | Y | N | N/A | N/A | |
| GW-96 | −8 | −0.1 | 0.1 | 250 | 55.5 | 32.7 | 5.4 | 1.4 | F | N | Y | N | N | |
| GW-97 | −11.5 | −0.23 | 6.62 | 700.0 | 50.3 | 38.8 | 9.2 | 1.6 | F | Y | N | N/A | N/A | |
| GW-98 | −9.5 | −0.53 | 0.53 | 75.0 | 40.6 | 36.4 | 21.4 | 1.4 | G | Y | N | N/A | N/A | |
| GW-99 | −8.2 | 0 | 0 | | NO SAMPLE TAKEN | | | | | | | | | |
| GW-100 | −9.6 | −0.15 | 0.06 | 110.0 | 35.5 | 35.1 | 29.5 | 2.2 | G | Y | N | N/A | N/A | |
| GW-101 | −8.2 | −0.15 | 0.06 | 0.0 | 35.5 | 35.1 | 27.6 | 1.5 | G | Y | N | N/A | N/A | |
| GW-102 | −13.5 | −0.05 | 0.11 | 2600.0 | 38.5 | 39.5 | 22.3 | 0.5 | F | N | Y | N | N | need hose clamp |
| GW-103 | −12.8 | 0 | 0.15 | 1200.0 | 36.0 | 33.7 | 28.8 | 1.2 | P | Y | N | N/A | N/A | |
| GW-104 | −13.5 | −8 | 0.15 | 1100.0 | 42.0 | 38.8 | 17.8 | 1.2 | G | Y | N | N/A | N/A | |
| GW-105 | −14.3 | −1.8 | 0.74 | 700.0 | 55.6 | 41.2 | 1.9 | 1.2 | F | Y | N | N/A | N/A | |
| GW-106 | −8 | 2.2 | 0.59 | 900 | 49 | 39 | 10.8 | 1 | G | Y | N | N/A | N/A | |
| GW-107 | −8 | 1.35 | 1.3 | 900 | 47 | 41 | 9.8 | 1.6 | G | Y | N | N/A | N/A | |
| GW-108 | −0.1 | 0 | 0.8 | 580.0 | 56.8 | 42.8 | 0.0 | 0.3 | F | Y | N | N/A | N/A | |
| GW-109 | −0.2 | 0 | 0.07 | 1025.0 | 56.9 | 42.7 | 0.0 | 0.4 | G | Y | N | N/A | N/A | |
| GW-110 | −9 | −0.33 | 0 | 50.0 | 27.9 | 30.6 | 39.4 | 1.6 | G | Y | N | N/A | N/A | |
| GW-111 | −4.5 | −0.5 | 0.15 | 1200.0 | 47.0 | 52.1 | 0.0 | 0.8 | G | Y | N | N/A | N/A | |
| GW-112 | −6 | −0.25 | 0.43 | 400.0 | 36.6 | 37.4 | 23.8 | 1.8 | G | Y | N | N/A | N/A | |
| GW-113 | −10 | −0.33 | 0.1 | 0.0 | 53.5 | 40.7 | 4.9 | 0.7 | G | Y | N | N/A | N/A | |
| GW-114 | −12.5 | −7.3 | 0.22 | 300.0 | 41.6 | 33.4 | 24.2 | 0.5 | G | Y | N | N/A | N/A | |

Horizontal Collection Trench (HCT)

| Device ID | | | | | | | | | | | | | | |
|---|---|---|---|---|---|---|---|---|---|---|---|---|---|---|
| HCT-91 | −20 | −20 | 0 | 0.0 | 52.9 | 32.5 | 11.5 | 3.0 | F | Y | N | N/A | N/A | |
| HCT-151 | −11.9 | −11.9 | 0.06 | 450.0 | 58.2 | 38.0 | 3.2 | 0.6 | G | Y | N | N/A | N/A | |
| HCT-201A | −6.8 | −6.1 | 0.140 | 200.0 | 47.4 | 33.6 | 16.1 | 2.2 | F | Y | N | N/A | N/A | |
| HCT-201B | −6.4 | −0.3 | 0.100 | 50.0 | 50.0 | 36.2 | 12.4 | 1.1 | F | Y | N | N/A | N/A | |
| HCT-202 | −6.8 | −5.3 | 0.420 | 50.0 | 46.0 | 32.8 | 17.7 | 3.5 | G | Y | N | N/A | N/A | |
| HCT-203 | −7.7 | −7.2 | 0.500 | 25.0 | 50.0 | 35.3 | 12.3 | 2.3 | F | Y | N | N/A | N/A | |
| HCT-205 | −8.2 | −7.3 | 0.150 | 125.0 | 50.8 | 36.0 | 10.5 | 2.5 | F | Y | N | N/A | N/A | |
| HCT-206 | −8.1 | −6 | 0.520 | 160.0 | 52.1 | 37.1 | 10.0 | 0.7 | F | Y | N | N/A | N/A | |
| HCT-207 | −7.4 | −0.6 | 0.100 | 150.0 | 48.9 | 35.0 | 13.2 | 2.6 | F | Y | N | N/A | N/A | |
| HCT-208 | −8.1 | −6.7 | 0.280 | 400.0 | 47.5 | 35.5 | 15.8 | 1.0 | F | Y | N | N/A | N/A | |

-continued

| | | | | | | | | | | |
|---|---|---|---|---|---|---|---|---|---|---|
| HCT-209 | −10 | −9.5 | 0.12 | 300 | 32 | 25.9 | 36.3 | 5.6 | G | Y | N | N/A | N/A | |
| HCT-210 | −9.9 | −9.6 | 0.1 | 200 | 54 | 42.2 | 2.8 | 1.2 | F | Y | N | N/A | N/A | |
| HCT-211 | −11.9 | −9.1 | 0.01 | 0 | 6 | 4.5 | 73.8 | 15.2 | F | Y | N | N/A | N/A | |
| HCT-213 | −11.7 | −9.7 | 0.19 | 1000 | 50 | 37 | 10.8 | 1.8 | F | Y | N | N/A | N/A | |
| HCT-214 | −12.6 | −0.6 | 0.35 | 300 | 46 | 38.8 | 12.2 | 3 | F | Y | N | N/A | N/A | |
| HCT-215 | −12.8 | −1.3 | 0.17 | 200 | 46 | 38.8 | 15.4 | 3.7 | F | Y | N | N/A | N/A | |
| HCT-216 | −12.3 | 0 | 0.1 | 0 | 43 | 35.2 | 17.7 | 4.2 | F | Y | N | N/A | N/A | |
| HCT-217 | −10.5 | −3.1 | 0.18 | 75 | 47 | 33.7 | 19.6 | 3.6 | F | Y | N | N/A | N/A | |
| HCT-218 | −12.9 | −7 | 0.18 | 600 | 53 | 37.8 | 7.4 | 2.1 | F | Y | N | N/A | N/A | |
| HCT-219 | −13.2 | −12.5 | 0.03 | 2000 | 44 | 35.2 | 18.4 | 2.5 | F | Y | N | N/A | N/A | |
| HCT-220 | −13.9 | −0.5 | 0.24 | 250 | 50 | 36.7 | 10.9 | 2.8 | P | Y | N | N/A | N/A | |
| HCT_221 | −12.6 | −11.2 | 0.4 | 0 | 14 | 32.3 | 44.8 | 0.7 | F | Y | N | N/A | N/A | |
| HCT-222 | −13.3 | −12.6 | 0.19 | 1050 | 30 | 36.6 | 29.4 | 3.5 | F | Y | N | N/A | N/A | |
| HCT-223 | 4 | 3 | 0.6 | 75 | 47 | 37.9 | 13.4 | 2 | F | Y | N | N/A | N/A | |
| | | | 5.13 | | | | | | | | | | | |
| Gas Wells | | | | | | | | | | | | | | |
| HCT-224 | −7.4 | −0.15 | 0.24 | 0 | 21 | 50.7 | 27.2 | 1 | G | Y | N | N/A | N/A | |
| HCT-225 | −12.5 | 0 | 0 | 1150 | 58 | 41.6 | 0 | 0.6 | P | Y | N | N/A | N/A | |
| HCT-226 | −13 | −13.1 | 0.08 | 375 | 48 | 41.5 | 8.3 | 2.2 | F | Y | N | N/A | N/A | |
| HCT-227 | −3.8 | −3.6 | 0.13 | 100 | 51 | 38.9 | 8.2 | 1.4 | G | Y | N | N/A | N/A | |
| HCT-228 | −9.7 | −9.5 | 0.06 | 710 | 52 | 40.2 | 5.6 | 1.7 | F | Y | N | N/A | N/A | |
| HCT-229 | −11.8 | −1.4 | 0.08 | 100 | 35 | 28.9 | 31.9 | 3.7 | G | Y | N | N/A | N/A | |
| HCT-230 | −13.7 | −5.3 | 0.27 | 100 | 34 | 26.2 | 34.3 | 5.4 | F | Y | N | N/A | N/A | |
| HCT-231 | −13 | −0.44 | 0.08 | 1150 | 41 | 40.8 | 15.5 | 2.3 | F | Y | N | N/A | N/A | |
| HCT-232 | −9.2 | −0.54 | 0.11 | 775 | 35 | 29.1 | 32.9 | 3 | G | Y | N | N/A | N/A | |
| HCT-233 | −10.7 | −0.51 | 4.56 | 700 | 35 | 31.3 | 31 | 2.7 | G | Y | N | N/A | N/A | |
| HCT-234 | −9.8 | −3.8 | 6.56 | 1450 | 38 | 33.1 | 27.3 | 1.8 | G | Y | N | N/A | N/A | |
| HCT-235 | −6.1 | −1.6 | 0.67 | 500 | 28 | 29.8 | 40.2 | 1.6 | G | Y | N | N/A | N/A | |
| HCT-236 | −10.8 | −3.7 | 0.23 | 0 | 34 | 27.6 | 33 | 4.8 | G | Y | N | N/A | N/A | |
| HCT-237 | 25 | | 0.15 | 0 | 48 | 35 | 13.9 | 3 | G | Y | N | N/A | N/A | WELL DOES NOT EXIST |
| HCT-238 | −10.8 | −4.5 | 0 | 200 | 46 | 40.6 | 10.1 | 1.6 | G | N | Y | Y | N | |
| HCT-239 | −9 | −0.13 | 0.01 | 100 | 36 | 34.2 | 26.3 | 2.9 | G | F | N | N/A | N/A | |
| HCT-240 | −10 | −0.3 | 0 | 0 | 3.3 | 2.4 | 74.1 | 19.2 | P | Y | N | N/A | N/A | FIX 2' Line |
| HCT-241 | −6.6 | −0.3 | 0.24 | 1750 | 57 | 52.6 | 6 | 0.5 | G | Y | N | N/A | N/A | |
| HCT-242 | −12.5 | −1.4 | 0.6 | 0 | 4.3 | 3.8 | 73.2 | 17.9 | G | Y | N | N/A | N/A | |
| HCT-243 | −11 | −0.4 | 0.24 | 10 | 49 | 36.4 | 4 | 1 | G | Y | N | N/A | N/A | |
| HCT-244 | −7.6 | −0.4 | 0.25 | 130 | 41 | 40.2 | 16.3 | 2.4 | G | Y | N | N/A | N/A | |
| HCT-245 | −7.3 | −0.1 | 0.7 | 400 | 38 | 38.6 | 20.5 | 2.3 | G | Y | N | N/A | N/A | |
| HCT-246 | −9.3 | −0.34 | 0.18 | 800 | 28 | 42.8 | 26.4 | 2.2 | G | Y | N | N/A | N/A | |
| HCT-247 | −9.9 | −23.3 | 0 | 0.0 | 20.7 | 52.2 | 25.5 | 1.3 | P | Y | Y | N | N | STEM LEAKS NON OP - |
| HCT-248 | −8 | | | 150.0 | 51.7 | 37.3 | 8.4 | 2.3 | G | Y | N | N/A | N/A | needs new valve |
| HCT-273 | −23.5 | | | | | | | | | | | | | |
| HCT-277 | −7.7 | −4.6 | 0.08 | 1750.0 | 34.0 | 41.8 | 2.7 | 1.3 | G | Y | N | N/A | N/A | |
| | | | 15.52 | | | | | | | | | | | |
| HCT-EC1 | −12.2 | −0.07 | 0 | 0.0 | NO SAMPLE TAKEN | | | | F | Y | N | N/A | N/A | needs hose clamp |
| HCT-EC2 | −13.6 | 0 | 0.11 | 55.5 | 39.0 | 4.3 | | 1.0 | G | Y | N | N/A | N/A | needs hose clamp |
| HCT-EC3 | −18 | −0.12 | 0 | NO SAMPLE TAKEN | | | | | F | Y | N | N/A | N/A | |
| HCT-EC4 | −17.6 | −0.51 | 0 | NO SAMPLE TAKEN | | | | | F | Y | N | N/A | N/A | |
| HCT-EC5 | −22 | −0.63 | 0 | NO SAMPLE TAKEN | | | | | F | Y | N | N/A | N/A | |
| HCT-EC6 | −20 | −0.37 | 0 | NO SAMPLE TAKEN | | | | | F | Y | N | N/A | N/A | |

| Device ID | | | | | | | | | | | | | | |
|---|---|---|---|---|---|---|---|---|---|---|---|---|---|---|
| HCT-EC7 | −20 | −0.01 | 0 | | NO SAMPLE TAKEN | | | | F | Y | N | N/A | N/A | |
| HCT-EC8 | −16.6 | 0 | 0 | | NO SAMPLE TAKEN | | | | F | Y | N | N/A | N/A | |
| HCT-EC9 | −15.2 | 0.22 | 0 | | NO SAMPLE TAKEN | | | | F | Y | N | N/A | N/A | |
| HCT-EC10 | −24 | 0 | 0 | | NO SAMPLE TAKEN | | | | F | Y | N | N/A | N/A | |

Cleanouts/Other

| Device ID | | | | | | | | | | | | | | |
|---|---|---|---|---|---|---|---|---|---|---|---|---|---|---|
| CT-1 | −13.4 | −13 | 0.7 | 2200.0 | 16.4 | 29.0 | 52.5 | 1.5 | G | 104 | N | — | — | |
| CT-24 | −31.5 | −9.8 | 0.04 | 540.0 | 40.1 | 33.1 | 23.5 | 3.0 | F | Y | N | — | — | |
| MSE-301 | −33.9 | −32.5 | 0.1 | 750.0 | 50.5 | 33.2 | 13.5 | 2.9 | F | Y | N | — | — | |
| MSE-302 | −34.2 | −33.3 | 0.25 | 370.0 | 49.5 | 33.5 | 14.4 | 2.4 | F | Y | N | — | — | |
| MSE-305 | −30 | −1 | 0 | 200.0 | 58.3 | 38.4 | 2.5 | 0.4 | F | Y | N | — | — | |
| S1P1CO | −32.9 | −31 | 0.06 | 0.0 | 45.2 | 28.2 | 23.4 | 2.1 | F | Y | N | — | — | |
| S1P1CON | −12.5 | −12.3 | 0 | 0.0 | 3.3 | 2.5 | 80.3 | 15.4 | P | Y | N | — | — | |
| S2P2COPK | −34.5 | −9.9 | 0.11 | 150.0 | 53.7 | 35.5 | 8.5 | 2.0 | P | Y | N | — | — | |
| S2P2COSL | −34.6 | −0.1 | 0.03 | 0.0 | 19.7 | 15.9 | 55.8 | 8.3 | P | Y | N | — | — | |
| S3CTB | −34.3 | −34.1 | 0 | 0.0 | 18.8 | 13.5 | 58.1 | 9.1 | F | Y | N | — | — | |
| S3CTD | −33.7 | −21 | 0.21 | 0.0 | 42.6 | 29.2 | 24.5 | 3.0 | F | Y | N | — | — | |
| S3COE | −30 | −7.3 | 0 | | NO SAMPLE TAKEN | | | | F | Y | N | — | — | |
| S3COF | −30 | −6.7 | 1.5 | | NO SAMPLE TAKEN | | | | F | Y | N | — | — | |

Gas Wells

| Device ID | | | | | | | | | | | | | | |
|---|---|---|---|---|---|---|---|---|---|---|---|---|---|---|
| S3SR | −31.8 | −0.5 | PLUGGED | 0.0 | 1.2 | 0.7 | 77.0 | 20.1 | F | Y | N | — | — | PLUGED PORT-NEEDS FIXED |
| S4P2CT | −8 | −6.1 | 0.15 | 100 | 36 | 30.7 | 30.3 | 2.4.G | | Y | N | — | — | |
| S4P2CT2 | −12.5 | 0 | 0 | | NO SAMPLE TAKEN | | | | G | Y | N | — | — | |
| S4P21 | −8.2 | −3.16 | 0.06 | 0.0 | 46.6 | 35.6 | 14.8 | 2.8 | F | Y | N | — | — | |
| S1P1PC03 | −10 | −4.6 | 0.05 | 0.0 | 27.8 | 22.1 | 43.3 | 6.4 | F | Y | N | — | — | |
| S1P2CO | −10 | −1.1 | 5.4 | 0.0 | 27.8 | 22.1 | 43.3 | 6.4 | G | Y | N | — | — | |
| S1P3CO | −9.4 | 0 | 2.6 | 0.0 | 53.2 | 41.4 | 3.9 | 1.4 | G | Y | N | — | — | |
| S4P2PCO1 | −9.3 | −8.6 | 0 | 0.0 | 13.6 | 10.7 | 64.5 | 10.6 | G | Y | N | — | — | |
| S4P2PCO2 | −8.7 | −0.45 | 0.06 | 200.0 | 28.9 | 24.3 | 41.7 | 5.0 | G | Y | N | — | — | |
| S4P2PCO3 | −10.7 | 0 | 0 | | NO SAMPLE TAKEN | | | | G | Y | N | — | — | |
| S2SECO | −20 | −17.6 | 0 | 0.0 | 56.8 | 36.0 | 24.5 | 1.4 | G | Y | N | — | — | |

Appendices B: GEM Reading to Mass Spectrometer Equivalent

| Date/time | | | | | |
|---|---|---|---|---|---|
| Jun. 24, 2016 1:50 PM | Mass Spec | 45 | 36.6 | 16.4 | 1.76 |
| Jun. 24, 2016 1:50 PM | GEM | 48.7 | 38.3 | 12.1 | 0.9 |
| | GEM/Mass Spec correction factor = | 0.924025 | 0.955614 | 1.355372 | 1.955556 |

Appendices C: Updated Results from Three-Four Week Ongoing Landfill Tuning

| | Flare vac | Flow in scfm | CH4 | CO2 | N2 | O2 | H2S | CH4 | CO2 | N2 | O2 |
|---|---|---|---|---|---|---|---|---|---|---|---|
| Jun. 24, 2016 13:50 | −38 | 2500 | 48.7 | 38.3 | 12.1 | 0.9 | | 44.9988 | 36.59948 | 16.3955 | 1.7595 |
| Jun. 27, 2016 11:09 | −38 | 2550 | 51.1 | 39.3 | 8.7 | 0.9 | | 47.2164 | 37.55508 | 11.7885 | 1.7595 |
| Jun. 27, 2016 16:16 | −38.5 | 2550 | 51.1 | 39.7 | 8.6 | 0.6 | | 47.2164 | 37.93732 | 11.653 | 1.173 |
| Jun. 28, 2016 9:07 | −39 | 2575 | 52.3 | 40.2 | 6.6 | 0.9 | | 48.3252 | 38.41512 | 8.943 | 1.7595 |
| Jun. 28, 2016 15:49 | −38 | 2580 | 52.9 | 39.6 | 6.8 | 0.7 | | 48.8796 | 37.84176 | 9.214 | 1.3685 |
| Jun. 29, 2016 10:07 | −38.5 | 2575 | 52.6 | 41.1 | 5.5 | 0.8 | | 48.6024 | 39.27516 | 7.4525 | 1.564 |
| Jun. 29, 2016 15:16 | −39 | 2550 | 53 | 40.7 | 5.7 | 0.6 | | 48.972 | 38.89292 | 7.7235 | 1.173 |
| Jun. 30, 2016 8:31 | −39 | 2550 | 53.1 | 40.1 | 6 | 0.8 | | 49.0644 | 38.31956 | 8.13 | 1.564 |
| Jun. 30, 2016 15:57 | −39 | 2600 | 53.8 | 38.8 | 6.8 | 0.6 | 750 ppm | 49.7112 | 37.07728 | 9.214 | 1.173 |
| Jul. 1, 2016 8:47 | −38.5 | 2550 | 54.2 | 40.5 | 4.8 | 0.5 | 650 ppm | 50.0808 | 38.7018 | 6.504 | 0.9775 |
| Jul. 1, 2016 15:24 | −38.5 | 2575 | 54.5 | 40 | 5 | 0.5 | | 50.358 | 38.224 | 6.775 | 0.9775 |
| Jul. 5, 2016 11:52 | −38 | 2580 | 54.3 | 40.6 | 4.5 | 0.6 | 700 ppm | 50.1732 | 38.79736 | 6.0975 | 1.173 |
| Jul. 11, 2016 10:35 | −38 | 2560 | 52.2 | 40.4 | 6.7 | 0.7 | 650 ppm | 48.2328 | 38.60624 | 9.0785 | 1.3685 |
| Jul. 11, 2016 15:52 | −39 | 2575 | 52.9 | 39.5 | 7.1 | 0.5 | | 48.8796 | 37.7462 | 9.6205 | 0.9775 |
| Jul. 12, 2016 11:31 | −40 | 2560 | 54.3 | 40.4 | 4.8 | 0.5 | | 50.1732 | 38.60624 | 6.504 | 0.9775 |
| Jul. 12, 2016 15:29 | −39 | 2575 | 53.9 | 38.8 | 6.9 | 0.4 | | 49.8036 | 37.07728 | 9.3495 | 0.782 |
| Jul. 14, 2016 10:30 | −39 | 2400 | 54.2 | 40.6 | 4.7 | 0.5 | | 50.0808 | 38.79736 | 6.3685 | 0.9775 |
| Jul. 14, 2016 16:10 | −39.5 | 2425 | 54.2 | 40 | 5.5 | 0.3 | | 50.0808 | 38.224 | 7.4525 | 0.5865 |
| Jul. 15, 2016 11:26 | −39 | 2300 | 53.9 | 41.2 | 4.4 | 0.5 | | 49.8036 | 39.37072 | 5.962 | 0.9775 |
| Jul. 15, 2016 15:40 | −39 | 2300 | 53.1 | 40.6 | 5.9 | 0.4 | | 49.0644 | 38.79736 | 7.9945 | 0.782 |
| Jul. 25, 2016 7:42 | −40 | 2250 | 55.7 | 41.1 | 2.8 | 0.4 | 700 ppm | 51.4668 | 39.27516 | 3.794 | 0.782 |

Although the invention has been explained in relation to its preferred embodiment, it is to be understood that many other possible modifications and variations can be made without departing from the spirit and scope of the invention as hereinafter claimed.

What is claimed is:

1. A method of reducing air intrusion from existing landfill gas collection systems comprises the steps of:

(A) providing a plurality of landfill gas wells and a gas collection system, wherein the plurality of landfill gas wells is in fluid communication with the gas collection system;

(B) collecting a plurality of gas-well samples from each of the plurality of landfill gas wells with a gas sample test unit;

(C) surveying each of the plurality of landfill gas wells in order to receive a gas well checklist results for each gas well, prompting to upload a gas well device identification, a type of wellhead, a vacuum source pressure, a well vacuum pressure and a pressure difference of orifice as the gas well checklist results, prompting to verify a plurality of gas well maintenance requirements with a preset specification for each of the plurality of gas well maintenance requirements as the gas well checklist results;

(D) receiving an on-field extracted gas quality report for each of the plurality of landfill gas wells with a field-grade landfill gas analyzer, providing an extracted on-field methane percentage reading, an extracted on-field carbon dioxide percentage reading, an extracted on-field nitrogen percentage reading and an extracted on-field oxygen percentage reading within the on-field extracted gas quality report;

(E) generating an off-field extracted gas quality report for each of the plurality of gas-well samples with a high-speed gas quality analyzer, providing an extracted off-field methane percentage reading, an extracted off-field carbon dioxide percentage reading, an extracted off-field nitrogen percentage reading and an extracted off-field oxygen percentage reading within the off-field extracted gas quality report;

(F) uploading the gas well checklist results, the on-field extracted gas quality report and the off-field extracted gas quality report from a computing device to a remote server, wherein the computing device is communicably couples the remote server to the field-grade landfill gas analyzer and the high-speed gas quality analyzer;

(G) collecting a plurality of collection gas testers from the gas collection system with the gas sample test unit;

(H) receiving an on-field collected gas quality report for the gas collection system with the field-grade landfill gas analyzer, providing a collected on-field methane percentage reading, a collected on-field carbon dioxide percentage reading, a collected on-field nitrogen percentage reading and a collected on-field oxygen percentage reading within the on-field collected gas quality report;

(I) generating an off-field collected gas quality report for each of the plurality of collection gas testers with the high-speed gas quality analyzer, providing a collected off-field methane percentage reading, a collected off-field carbon dioxide percentage reading, a collected off-field nitrogen percentage reading and a collected off-field oxygen percentage reading within the off-field collected gas quality report;

(J) uploading the on-field collected gas quality report and the off-field collected gas quality report from the computing device to the remote server; and (K) generating a well-adjustment report for the plurality of landfill gas wells with the remote server from the remote server from the gas well checklist results, the on-field extracted gas quality report, the off-field extracted gas quality report, the on-field collected gas quality report and the off-field collected gas quality report, recording an extracted gas correction factor for methane within the well-adjustment report, recording an extracted gas correction factor for carbon dioxide within the well-adjustment report, recording an extracted gas correction factor for nitrogen within the well-adjustment report, recording an extracted gas correction factor for oxygen within the well-adjustment report, recording a collected gas correction factor for methane within the well-adjustment report, recording a collected gas correction factor for carbon dioxide within the well-adjustment report, recording a collected gas correction factor for nitrogen within the well-adjustment report, recording a collected gas correction factor for oxygen within the well-adjustment report.

2. The method of reducing air intrusion from existing landfill gas collection systems as claimed in claim 1 comprises the steps of:
prompting to repair a specific gas well from the plurality of landfill gas wells,
if an irregularity is identified between one of the plurality of gas well maintenance requirements and the corresponding preset specification for the specific gas well.

3. The method of reducing air intrusion from existing landfill gas collection systems as claimed in claim 1 comprises the steps of:
receiving the extracted on-field methane percentage reading for each of the plurality of landfill gas wells from the field-grade landfill gas analyzer;
receiving the extracted on-field carbon dioxide percentage reading for each of the plurality of landfill gas wells from the field-grade landfill gas analyzer;
receiving the extracted on-field nitrogen percentage reading for each of the plurality of landfill gas wells from the field-grade landfill gas analyzer; and
receiving the extracted on-field oxygen percentage reading for each of the plurality of landfill gas wells from the field-grade landfill gas analyzer.

4. The method of reducing air intrusion from existing landfill gas collection systems as claimed in claim 1 comprises the steps of:
receiving the extracted off-field methane percentage reading for each of the plurality of landfill gas wells from the high-speed gas quality analyzer;
receiving the extracted off-field carbon dioxide percentage reading for each of the plurality of landfill gas wells from the high-speed gas quality analyzer;
receiving the extracted off-field nitrogen percentage reading for each of the plurality of landfill gas wells from the high-speed gas quality analyzer; and
receiving the extracted off-field oxygen percentage reading for each of the plurality of landfill gas wells from the high-speed gas quality analyzer.

5. The method of reducing air intrusion from existing landfill gas collection systems as claimed in claim 1 comprises the steps of:
receiving the collected on-field methane percentage reading for the gas collection system from the field-grade landfill gas analyzer;
receiving the collected on-field carbon dioxide percentage reading for the gas collection system from the field-grade landfill gas analyzer;
receiving the collected on-field nitrogen percentage reading for the gas collection system from the field-grade landfill gas analyzer; and
receiving the collected on-field oxygen percentage reading for the gas collection system from the field-grade landfill gas analyzer.

6. The method of reducing air intrusion from existing landfill gas collection systems as claimed in claim 1 comprises the steps of:
receiving the collected off-field methane percentage reading for the gas collection system from the high-speed gas quality analyzer;
receiving the collected off-field carbon dioxide percentage reading for the gas collection system from the high-speed gas quality analyzer;
receiving the collected off-field nitrogen percentage reading for the gas collection system from the high-speed gas quality analyzer; and
receiving the collected off-field oxygen percentage reading for the gas collection system from the high-speed gas quality analyzer.

7. The method of reducing air intrusion from existing landfill gas collection systems as claimed in claim 1 comprises the steps of:
providing an extracted on-field methane percentage reading as the on-field extracted gas quality report;
providing an extracted off-field methane percentage reading as the off-field extracted gas quality report; and
comparing the extracted on-field methane percentage reading to the extracted off-field methane percentage reading with the remote server in order to compute the extracted gas correction factor for methane.

8. The method of reducing air intrusion from existing landfill gas collection systems as claimed in claim 1 comprises the steps of:
providing an extracted on-field carbon dioxide percentage reading as the on-field extracted gas quality report;
providing an extracted off-field carbon dioxide percentage reading as the off-field extracted gas quality report; and
comparing the extracted on-field carbon dioxide percentage reading to the extracted off-field carbon dioxide percentage reading with the remote server in order to compute the extracted gas correction factor for carbon dioxide.

9. The method of reducing air intrusion from existing landfill gas collection systems as claimed in claim 1 comprises the steps of:
providing an extracted on-field nitrogen percentage reading as the on-field extracted gas quality report;
providing an extracted off-field nitrogen percentage reading as the off-field extracted gas quality report; and
comparing the extracted on-field nitrogen percentage reading to the extracted off-field nitrogen percentage reading with the remote server in order to compute the extracted gas correction factor for nitrogen.

10. The method of reducing air intrusion from existing landfill gas collection systems as claimed in claim 1 comprises the steps of:
providing an extracted on-field oxygen percentage reading as the on-field extracted gas quality report;
providing an extracted off-field oxygen percentage reading as the off-field extracted gas quality report; and
comparing the extracted on-field oxygen percentage reading to the extracted off-field oxygen percentage reading with the remote server in order to compute the extracted gas correction factor for oxygen.

11. The method of reducing air intrusion from existing landfill gas collection systems as claimed in claim 1 comprises the steps of:
providing a collected on-field methane percentage reading as the on-field collected gas quality report;
providing a collected off-field methane percentage reading as the off-field collected gas quality report; and
comparing the collected on-field methane percentage reading to the collected off-field methane percentage reading with the remote server in order to compute the collected gas correction factor for methane.

12. The method of reducing air intrusion from existing landfill gas collection systems as claimed in claim 1 comprises the steps of:
providing a collected on-field carbon dioxide percentage reading as the on-field collected gas quality report;
providing a collected off-field carbon dioxide percentage reading as the off-field collected gas quality report; and
comparing the collected on-field carbon dioxide percentage reading to the collected off-field carbon dioxide percentage reading with the remote server in order to compute the collected gas correction factor for carbon dioxide.

13. The method of reducing air intrusion from existing landfill gas collection systems as claimed in claim 1 comprises the steps of:
providing a collected on-field nitrogen percentage reading as the on-field collected gas quality report;
providing a collected off-field nitrogen percentage reading as the off-field collected gas quality report; and
comparing the collected on-field nitrogen percentage reading to the collected off-field nitrogen percentage reading with the remote server in order to compute the collected gas correction factor for nitrogen.

14. The method of reducing air intrusion from existing landfill gas collection systems as claimed in claim 1 comprises the steps of:
providing a collected on-field oxygen percentage reading as the on-field collected gas quality report;
providing a collected off-field oxygen percentage reading as the off-field collected gas quality report; and
comparing the collected on-field oxygen percentage reading to the collected off-field oxygen percentage reading with the remote server in order to compute the collected gas correction factor for oxygen.

15. The method of reducing air intrusion from existing landfill gas collection systems as claimed in claim 1 comprises the steps of:
uploading a positive pressure, wherein the positive pressure is uploaded as a well vacuum pressure of the gas well checklist results;
identifying a specific well number, wherein the specific well number is uploaded as a gas well device identification of the corresponding gas well checklist results; and
prompting a negative pressure adjustment for a well head of the corresponding landfill gas well associated with the specific well number, wherein the negative pressure adjustment is recorded within the well-adjustment report.

16. The method of reducing air intrusion from existing landfill gas collection systems as claimed in claim 1 comprises the steps of:
providing a collected off-field methane percentage reading as the off-field collected gas quality report;
designating the collected off-field methane percentage reading as a preset methane percentage;
receiving a first negative pressure, wherein the first negative pressure is uploaded as a vacuum source pressure within the gas well checklist results;
receiving a second negative pressure, wherein the second negative pressure is uploaded as a well vacuum pressure within the gas well checklist results;
generating a well-head open request for each of the plurality of landfill gas wells,
if an extracted off-field methane percentage reading of the off-field extracted gas quality report is greater than the preset methane percentage; and
recording the well-head open request with the well-adjustment report.

17. The method of reducing air intrusion from existing landfill gas collection systems as claimed in claim 1 comprises the steps of:
providing a collected off-field methane percentage reading as the off-field collected gas quality report;
designating the collected off-field methane percentage reading as a preset methane percentage;
receiving a first negative pressure, wherein the first negative pressure is uploaded as a vacuum source pressure within the gas well checklist results;
receiving a second negative pressure, wherein the second negative pressure is uploaded as a well vacuum pressure within the gas well checklist results;
generating a well-head close request for each of the plurality of landfill gas wells,
if an extracted off-field methane percentage reading of the off-field extracted gas quality report is lower than the preset methane percentage; and recording the well-head close request with the well-adjustment report.

18. The method of reducing air intrusion from existing landfill gas collection systems as claimed in claim 1 comprises the steps of:
repeating step (D) and step (H) in order to generate a plurality of flow-up adjustment reports for the plurality of landfill gas wells with the remote server.

19. The method of reducing air intrusion from existing landfill gas collection systems as claimed in claim 1 comprises the steps of:
providing an extracted on-field hydrogen sulfide parts per million (ppm) reading within the on-field extracted gas quality report and the on-field collected gas quality report;
receiving the extracted on-field hydrogen sulfide ppm reading for each of the plurality of landfill gas wells from a hydrogen sulfide gas analyzer;
receiving the collected on-field hydrogen sulfide ppm reading for the gas collection system from the hydrogen sulfide gas analyzer; and
generating a landfill well profile map of hydrogen sulfide from the extracted on-field hydrogen sulfide ppm reading for each of the plurality of landfill gas wells.

20. The method of reducing air intrusion from existing landfill gas collection systems as claimed in claim 1 comprises the steps of:
providing an extracted off-field hydrogen sulfide parts per million (ppm) reading within the off-field extracted gas quality report and the off-field collected gas quality report;
receiving the extracted off-field hydrogen sulfide ppm reading for each of the plurality of landfill gas wells from a hydrogen sulfide gas analyzer;
receiving the collected off-field hydrogen sulfide ppm reading for the gas collection system from the hydrogen sulfide gas analyzer; and
generating a landfill well profile map of hydrogen sulfide from the extracted off-field hydrogen sulfide ppm reading for each of the plurality of landfill gas wells.

* * * * *